(12) United States Patent
Sproch

(10) Patent No.: US 7,047,171 B1
(45) Date of Patent: May 16, 2006

(54) METHOD FOR THE CHARACTERIZATION OF THE THREE-DIMENSIONAL STRUCTURE OF PROTEINS EMPLOYING MASS SPECTROMETRIC ANALYSIS AND COMPUTATIONAL FEEDBACK MODELING

(76) Inventor: Norman K. Sproch, P.O. Box 41086, Tucson, AZ (US) 85717

( * ) Notice: Subject to any disclaimer, the term of this patent is extended or adjusted under 35 U.S.C. 154(b) by 0 days.

(21) Appl. No.: 09/287,307

(22) Filed: Apr. 7, 1999

Related U.S. Application Data

(63) Continuation-in-part of application No. 08/569,358, filed on Dec. 8, 1995, now abandoned.

(51) Int. Cl.
*G06F 17/50* (2006.01)
*H01J 49/04* (2006.01)

(52) U.S. Cl. ................ 703/12; 703/2; 250/288

(58) Field of Classification Search .......... 703/2, 703/5, 3, 12; 435/4, 6, 7.1; 702/22, 27; 250/288, 281, 282
See application file for complete search history.

(56) References Cited

U.S. PATENT DOCUMENTS

| | | | |
|---|---|---|---|
| 3,767,900 A | 10/1973 | Chao et al. | |
| 3,840,742 A | 10/1974 | Bell | 250/288 |
| 4,104,275 A | 8/1978 | Kauer | 260/297 |
| 4,209,698 A | 6/1980 | Hoppe | 250/281 |
| 4,271,425 A | 6/1981 | Wong | 357/72 |
| 4,367,072 A | 1/1983 | Vogtle et al. | 436/501 |
| 4,436,923 A | 3/1984 | Pacey et al. | 549/352 |
| 4,531,056 A | 7/1985 | Labowsky et al. | 250/288 |
| 4,542,293 A | 9/1985 | Fenn et al. | 250/288 |
| 4,838,274 A | 6/1989 | Schweighardt et al. | 128/654 |
| 4,842,701 A | 6/1989 | Smith et al. | 204/180 |
| 4,885,076 A | 12/1989 | Smith et al. | 204/299 |
| 4,935,624 A | 6/1990 | Henion et al. | 250/288 |
| 4,977,320 A | 12/1990 | Chowdhury et al. | 250/288 |
| 4,999,493 A | 3/1991 | Allen et al. | 250/288 |
| 5,005,147 A | 4/1991 | Krishen et al. | |
| 5,015,845 A | 5/1991 | Allen et al. | 250/288 |
| 5,067,099 A | 11/1991 | McCown et al. | |
| 5,068,098 A | 11/1991 | Schweighardt et al. | 424/9 |
| 5,071,581 A | 12/1991 | Cipriano | 252/77 |
| 5,078,097 A | 1/1992 | Chisholm | 73/61.1 C |
| 5,115,131 A | 5/1992 | Jorgenson et al. | 250/288 |
| 5,122,670 A | 6/1992 | Mylchreest et al. | 250/423 |
| 5,136,161 A | 8/1992 | Logan | 250/293 |
| 5,157,260 A | 10/1992 | Mylchreest et al. | 250/423 R |
| 5,170,053 A | 12/1992 | Hall et al. | 250/288 |
| 5,171,990 A | 12/1992 | Mylchreest et al. | 250/288 |
| 5,196,348 A | 3/1993 | Schweighardt et al. | 436/173 |
| 5,218,299 A | 6/1993 | Dunkel | |
| 5,223,226 A | 6/1993 | Wittmer et al. | 422/100 |
| 5,223,409 A * | 6/1993 | Ladner et al. | 435/69.7 |
| 5,245,186 A | 9/1993 | Chait et al. | 250/288 |
| 5,504,327 A * | 4/1996 | Sproch et al. | 250/288 |
| 5,504,672 A | 4/1996 | Hardiman et al. | |
| 5,572,125 A * | 11/1996 | Dunkel | 324/307 |
| 5,612,895 A * | 3/1997 | Balaji et al. | 364/496 |
| 5,708,593 A | 1/1998 | Saby et al. | 364/571.04 |

(Continued)

Primary Examiner—Thai Phan
(74) Attorney, Agent, or Firm—Quarles & Brady Streich Lang, LLP; Gavin J. Milczarek-Desai

(57) ABSTRACT

A method for characterizing the three-dimensional surface structure of molecules, particularly proteins and protein complexes, employing mass spectrometric analysis, an electrospray ionization (ES) source, a novel data interpretation process that utilizes comparisons of particular binding constants ($K_B$) and heats of formation ($\Delta H_f$), and computational feedback modeling.

12 Claims, 20 Drawing Sheets

U.S. PATENT DOCUMENTS

| | | | |
|---|---|---|---|
| 5,770,857 A * | 6/1998 | Fuerstenau et al. | 250/281 |
| 5,915,230 A * | 6/1999 | Berne et al. | 702/22 |
| 5,965,352 A * | 10/1999 | Stoughton et al. | 435/4 |
| 6,269,312 B1 * | 7/2001 | Mayo et al. | 702/19 |
| 6,434,490 B1 * | 8/2002 | Agrafiotis et al. | 702/27 |
| 2002/0150926 A1 * | 10/2002 | Jindal et al. | |

* cited by examiner

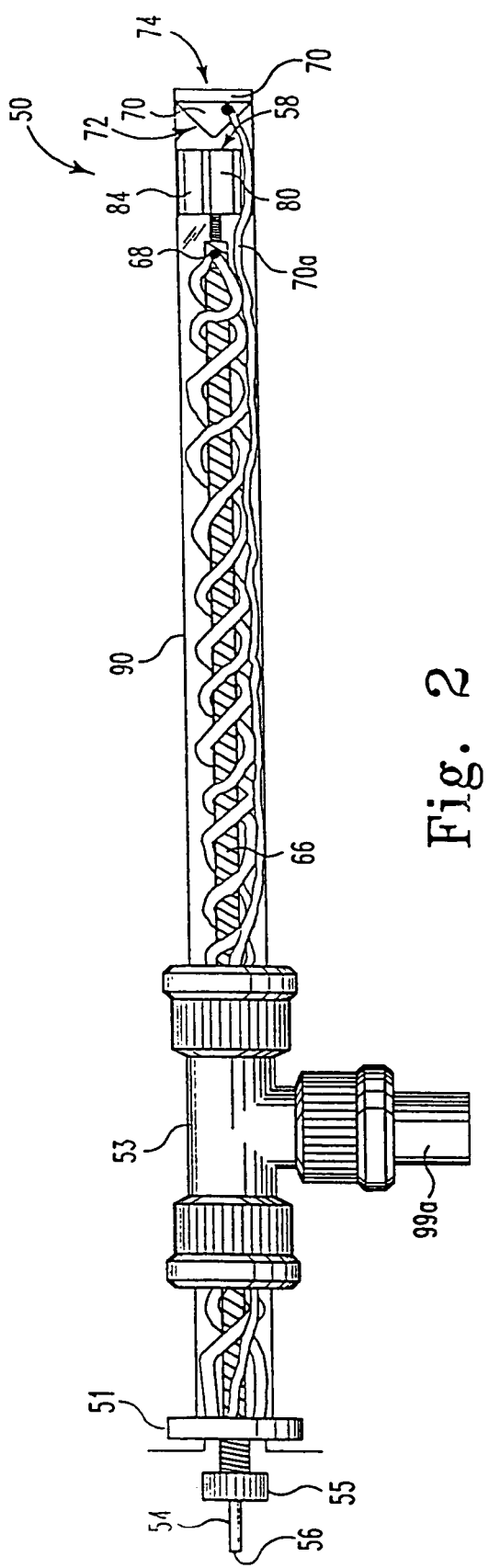
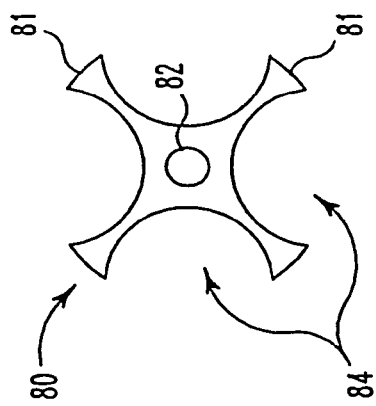
Fig. 2
Fig. 3

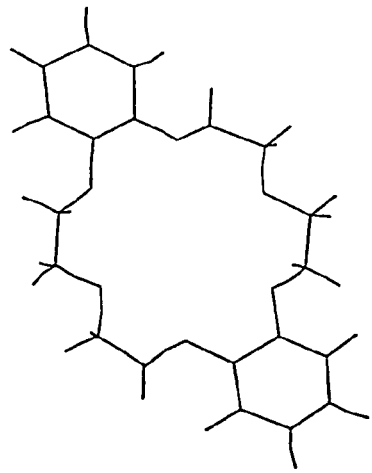
Fig. 17C Dibenzo-18-crown-6
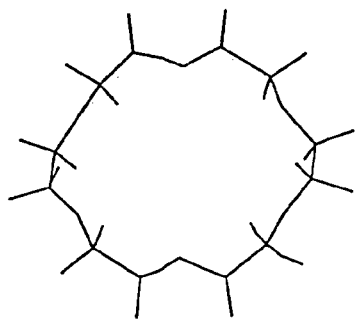
Fig. 17B 18-crown-6
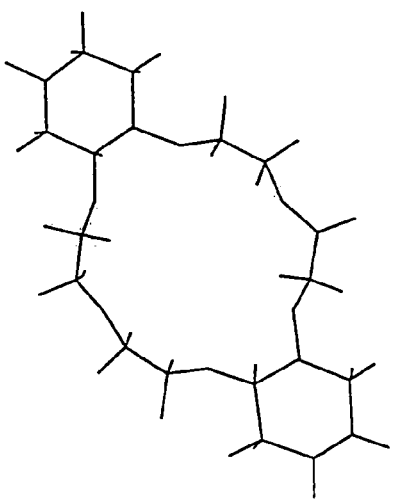
Fig. 17A Dicyclohexyl-18-crown-6
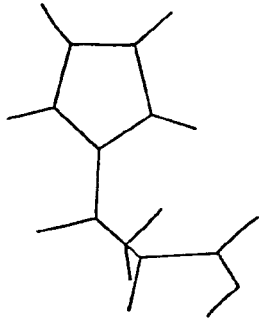
Fig. 18C Histidine$^+$
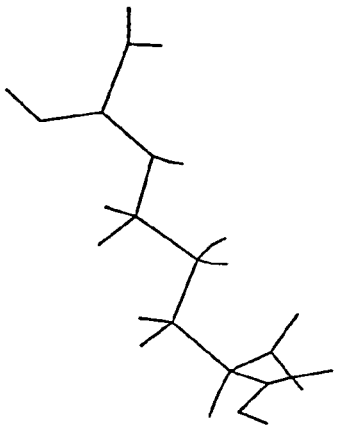
Fig. 18B Arginine$^+$
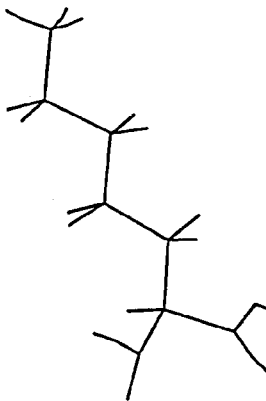
Fig. 18A Lysine$^+$

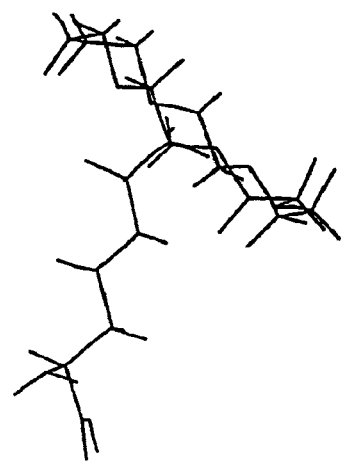
Fig. 20A 18-Crown-6/Lys
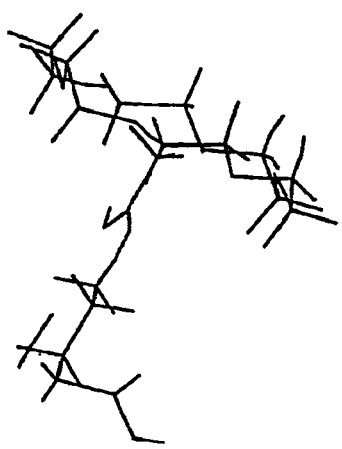
Fig. 20B 18-Crown-6/Arg
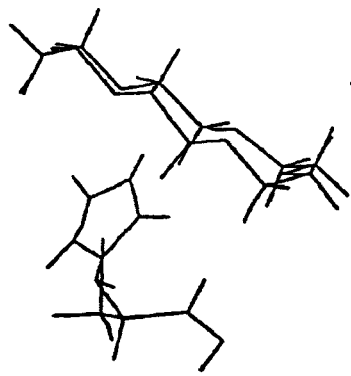
Fig. 20C 18-Crown-6/His
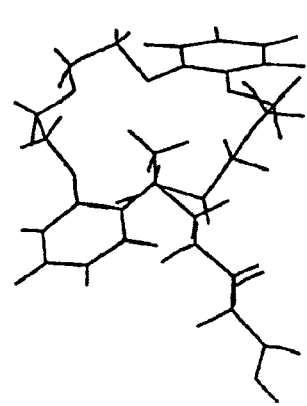
Fig. 20D Dibenzo-18-Crown-6/Lys+
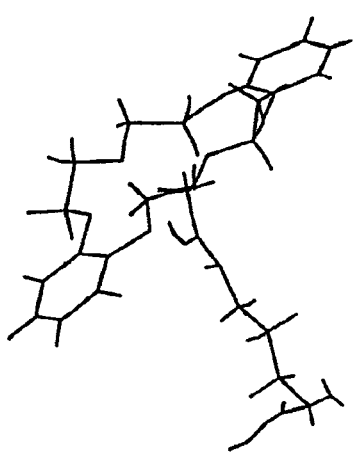
Fig. 20E Dibenzo-18-Crown-6/Arg+
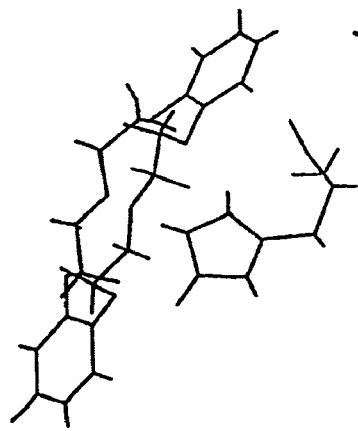
Fig. 20F Dibenzo-18-Crown-6/His

METHOD FOR THE CHARACTERIZATION OF THE THREE-DIMENSIONAL STRUCTURE OF PROTEINS EMPLOYING MASS SPECTROMETRIC ANALYSIS AND COMPUTATIONAL FEEDBACK MODELING

REFERENCE TO RELATED APPLICATIONS

This application is a continuation-in-part application of U.S. Ser. No. 08/569,358, filed on Dec. 8, 1995, now abandoned.

BACKGROUND OF THE INVENTION

1. Field of Invention

The present invention relates to methods for characterization of the structure of molecules and, more particularly, to a method for characterizing the three-dimensional surface structure of proteins and protein complexes employing electrospray mass spectrometric analysis (ES-MS) techniques and computational feedback modeling.

2. Description of the Prior Art

The employment of mass spectrometry for identification of chemical structures, molecular weights, determination of mixtures, and quantitative elemental analysis, based on the application of the mass spectrometer, is a known analytical technique. Mass spectrometry may be used to accurately determine the molecular weights and structural information of organic molecules based on the augmentation pattern of molecular ions formed when the molecule undergoes ionization and fragmentation. The mass of molecules may be measured by ionizing the molecules and measuring their trajectories in response to electric and/or magnetic fields in a vacuum.

Organic molecules having a molecular weight of about a few hundred to a few thousand Daltons are of great medical and commercial interest as they include, for example, polypeptides, proteins, DNA, RNA, oligosaccharides, and other macromolecules such as polymers thereof and other useful polymers. Any organic, organometallic, or other molecule may be analyzed by ES/MS. But of most interest are molecules with molecular weights over about 10,000 Daltons. "Electrospray" ionization is amenable to any type of mass spectrometry, and is therefore of considerable utility.

Electrospray mass spectrometry (ES/MS) has more recently been recognized as a significant tool used in the study of proteins and protein complexes. Electrospray ionization as a method of sample introduction for mass spectrometric analysis is also known. Generally, electrospray ionization is a method whereby ions are formed at atmospheric pressure and then introduced into a mass spectrometer using a special interface. In electrospray ionization, a sample solution containing molecules of interest and a solvent is typically pumped through a needle or small conductive tube and into an electrospray interface. An electrical potential of several kilovolts may be applied to the needle for generating a fine spray of charged droplets. The droplets may be sprayed at atmospheric pressure into a desolvation tube or chamber containing a heated gas to vaporize the solvent. Alternatively, the needle may extend into an evacuated chamber, and the sprayed droplets then desolvated in the evacuated chamber. The fine spray of highly charged droplets releases molecular ions as the droplets are desolvated. In either case, ions are focused into a beam, which is accelerated by an electric field gradient, and then analyzed in a mass spectrometer.

Because electrospray ionization occurs directly from solution at atmospheric pressure, the ions formed in this process tend to be strongly solvated. To carry out meaningful mass measurements, it is necessary that any solvent molecules attached to the ions be efficiently removed, that is, the molecules of interest must be "desolvated." In the prior art, desolvation is achieved in one way by interacting the droplets and solvated ions with a strong countercurrent flow (6–9 l/m) of a heated gas before the ions enter into the vacuum of the mass analyzer.

The use of such a strong countercurrent gas flow is expensive and difficult to operate because the gas flow rate and the temperature need to be controlled precisely and be optimized for each analyte and solvent system. If proper gas flow and temperature conditions are not attained, it can result in either an incomplete desolvation of the ions or a decrease in sensitivity as ions may be swept away by the gas at high flow rate. To enhance the desolvation process, some have used collisional activation by applying an electrostatic field in a region of reduced pressure between the sampling orifice of the mass analyzer and the skimmer.

Although high speed pumping is commonly incorporated to allow for the direct sampling of electrosprayed ions into the mass analyzer, the detailed method of ion transport from atmospheric pressure to vacuum is different in each case. Thus ion transport has been achieved through a 0.2 mm bore 60 mm long glass capillary tube and skimmer and a 1.0 mm diameter sampling orifice=and skimmer.

Techniques involving automated analysis and correction of light or magnetic-based spectral data also are well known in art. For example, Dunkel in U.S. Pat. No. 5,572,125 describes a method and system of using regression analysis to correct spectral data for various types of "noise," such as signal drift, sample saturation, removal of phase, or shim distortions. This method comprises the steps of providing experimental data to the system, initializing and running a simulation model of the experiment, comparing the simulated results with the experimental data, estimating the unknown parameters, and adjusting the simulated data to fit to the experimental model by employing regression analysis to correct the data in an iterative manner until predetermined criteria are met. However, this method does not disclose or suggest a method by which the three dimensional structures of protein or other large molecules may be determined.

Despite the advances in the sensitivity and resolution of spectrometric data made possible by improved sample introduction, desolvation, and data correction methods, very little attention has focused on the final analysis of spectrometric data in terms of determining the three-dimensional conformation of molecular complexes. Thus, a need exists for an effective method employing ES-MS techniques to characterize the surface structure of a molecule, particularly a protein or protein/small molecule complex. Presently, such a method has not been known.

SUMMARY OF THE INVENTION

This invention provides a method for characterizing the three-dimensional surface structure of molecules, particularly proteins and protein complexes, employing mass spectrometric analysis, an electrospray ionization (ES) source, a novel data interpretation process utilizing comparisons of particular binding constants ($K_B$) and heats of formation ($\Delta H_f$), and computational feedback modeling to refine the three-dimensional model created by such comparisons.

The invention particularly described and claimed herein is a method for characterizing the three-dimensional structure of a protein molecule comprising mixing a small molecule with a protein so that the small molecule binds non-covalently to the protein to form a protein-small molecule complex, performing electrospray ionization mass spectrometry (ES-MS) to obtain the spectrum of the protein-small molecule complex, using the spectrum so obtained to calculate the binding constant ($K_B$) for the binding of the small molecule to the protein, repeating the aforementioned steps with additional different small molecules, calculating the heat of formation ($\Delta H_f$) for the binding of each of the small molecules to a selected residue on the surface of the protein, calculating the heat of formation ($\Delta H_f$) for the binding of the small molecules to other selected residues on the surface of the protein, comparing the experimentally determined binding constants ($K_B$) with the calculated heats of formation ($\Delta H_f$), and utilizing these comparisons to characterize the three-dimensional structure of the protein. The molecular model elucidated through these comparisons are then further refined using experimental/computational feedback modeling. Such a method comprises the steps of: (a) performing a physical experiment on a predetermined system; (b) acquiring raw experimental data with selected instrumentation and digitizing the data (the raw experimental data may consist of a few or a very large number of datum); (c) storing the digitized data in a computer memory; (d) initializing and running a preselected computer program for modeling or simulating the physical experiment being performed in the initial step (a); (e) using the digitized experimental data to compute a new result for the computer simulation of the experiment, the results of which are also stored in a computer memory; (f) comparing the new result from the simulation with the digitized data derived from the physical experiment; (g) replacing the undefined parameters from the experiment with the explicit parameters assumed in the computer simulation, if the result is found to be within a predetermined parameter; and (h) if the result is found to be outside a predetermined parameter, establishing a feedback loop and initiating an iterative subroutine whereby the computer simulation adjusts itself, in an incremental way, to fit the simulation to the experimental value, compares the result to the experimental results after each computational step and feeds the experimental data back into the input loop of the computer simulation until the result of the comparison is found to be within the predetermined parameter.

More than one molecule may be bound to the protein surface during an experimental determination of ($K_B$). This would allow multiple binding constants ($K_B$) to be determined during one experiment. The method for novel data interpretation of electrospray mass spectrometry provided by this invention can unlock secrets to the structures of molecules and molecular complexes.

Hence, this novel ES/MS method opens the door to a wealth of new methods and applications that heretofore were unknown to the field. More specifically, this method provides a foundation for novel data interpretations of ES results to reveal characteristic structural features of molecules and molecular complexes, particularly proteins.

The ES probe of this invention is the subject of U.S. Pat. No. 5,504,327 (hereafter, "the '327 patent"), for which I am a co-inventor. The ES assembly is defined by a simple, economical, and efficient electrospray ionization interface constructed in the configuration of a probe that makes use of a standard 0.5 inch (13 mm) vacuum lock commonly found on conventional mass spectrometers. No modifications to the standard removable ion volume electron ionization/chemical ionization lens assembly of the mass spectrometer are required to obtain excellent results.

The '327 patent is also directed at methods for introducing desolvated or partially desolvated ionized molecules of interest into a mass spectrometer for analysis and certain methods for characterizing the three-dimensional structure of a protein molecule. This application is directed to a further method for characterizing the three-dimensional surface structure of a protein or protein complex. As discussed below, the manner by which the protein surface is modified has been initially confirmed by experimentation to show that the crown ethers bind primarily to three amino acids located on the protein surface. This is a valuable discovery in that virtually all drugs work by modifying the structure of proteins, and thereby their function, in some manner at the molecular level.

More particularly, the electrospray ionization (ES) probe assembly introduces a sample of ions into a mass spectrometer for mass spectrometric analysis comprising desolvation means having an entrance orifice and an exit orifice, means for applying a voltage to the desolvation means, means for controllably heating the desolvation means, means for measuring the temperature of the desolvation means, skimmer means for focusing and directing the ions to the mass spectrometer, lens means positioned before the skimmer means for initially focusing the ions prior to their entering the skimmer means, and an evacuable transparent dielectric encasement for housing the components of the probe assembly.

The sample of ions is initially generated by electrospray means generating a spray of charged droplets containing the molecules, or molecular complexes of interest, and solvent. The skimmer means is provided with an axial orifice extending therethrough electrically isolated from the desolvation means and positioned at a distance from the exit orifice of the desolvation means. The lens means comprises spacer means threadably affixed to the desolvation means adjacent the exit orifice thereof by an adjustable engagement for transporting and focusing the ions of interest.

Also described herein is a system for analyzing the mass spectra of molecules and molecular complexes of interest comprising a mass spectrometer having an inlet orifice for receiving therein ionized molecules of interest and molecular complexes, and an electrospray ion source coupled to the mass spectrometer for introducing ionized molecules of interest and molecular complexes therein for analysis. The electrospray ion source of this system includes a source of a dilute solution of the molecules of interest, electrospray means for generating a fine spray of tiny charged droplets of said solution, means for imposing a first voltage on the electrospray means, a capillary tube having an entrance orifice positioned across a gap from the electrospray means for receiving the charged droplets and an exit orifice for the ionized molecules of interest, means for imposing a second voltage on the capillary tube, means for controllably heating the capillary tube, a sampling cone for directing the ionized molecules of interest to the mass spectrometer, lens means positioned before the sampling cone for initially focusing the ionized molecules prior to their entering the sampling cone, an evacuable tubular transparent dielectric encasing for housing the capillary tube, heating means, thermocouple means, sampling cone, and lens means, and means for creating a vacuum in the mass spectrometer and evacuable encasing. The mass spectrometer has a vacuum chamber forming the inlet orifice that forms a vacuum seal with the evacuable encasement adjacent the outlet side of the sampling cone. The source of a dilute solution of molecules of interest includes a syringe needle tube through which the solution is transferred to the electrospray means. The syringe needle is positioned a short distance from an entrance orifice of the capillary tube.

Even further described is a method for introducing desolvated or partially desolvated ionized molecules of interest into a mass spectrometer for analysis generally comprising the steps of creating a dilute solution of molecules of interest in a solvent, generating a fine spray of tiny droplets of the dilute solution of molecules and solvent, charging the tiny droplets, providing a desolvation tube having an entrance orifice and an exit orifice, positioning the entrance orifice of the desolvation tube adjacent the point of generation of the fine spray of tiny charged droplets, applying a voltage to the desolvation tube, receiving the charged droplets in the entrance orifice of the desolvation tube, transporting the droplets to the exit orifice of the desolvation tube, controllably heating the desolvation tube to substantially desolvate the droplets during their transport therethrough to provide ionized molecules of interest at the exit orifice of the desolvation tube, focusing the ionized molecules after their exiting the desolvation tube, and directing the focused ionized molecules of interest upon their exit from the focusing means through a skimmer means to remove inadequately ionized molecules of interest.

Also described in the '327 patent and herein is a method for characterizing the three-dimensional structure of a protein molecule comprising creating a dilute solution of protein molecules and molecular complexes of interest in a solvent, adding a predetermined amount of crown ethers to the solution so that the smaller crown ether molecules bind to the large protein molecules, charging the tiny droplets, generating a fine spray of tiny droplets of the solution of protein molecule-crown ether complexes and solvent, providing a desolvation tube having an entrance orifice and an exit orifice, positioning the entrance orifice of the desolvation tube adjacent the point of generation of the fine spray of tiny droplets, applying a voltage to the desolvation tube, receiving the charged droplets in the entrance orifice of the desolvation tube, transporting the droplets to the exit orifice of the desolvation tube, controllably heating the desolvation tube to substantially desolvate the droplets during their transport therethrough to provide ionized protein molecules at the exit orifice of the desolvation tube, focusing the ionized protein molecule-crown ether complexes after exiting the desolvation tube, and directing the focused ionized protein molecule-crown ether complexes upon their exit from the focusing means through a skimmer means to remove inadequately ionized protein molecule-crown ether complexes.

Other features and advantages of the invention will be apparent from the drawings and a more detailed description that follows.

BRIEF DESCRIPTION OF THE DRAWINGS

FIG. 2 is a side plane view of the electrospray ionization probe assembly provided by this invention;

FIG. 3 is a top plane view of a lens focusing means of the electrospray ionization probe assembly provided by this invention;

FIGS. 17A–17C represent the stick molecular structures of three crown ethers, dicyclohexano-1a-crown-6, 18-crown-6, and dibenzo-18-crown-6;

FIGS. 18A–18C represent the stick molecular structures of three protonated amino acid residues of interest, lysine, arginine and histidine;

FIGS. 20A–20F present the optimized molecular structures modeling the complexes of protonated amino acids with 18-crown-6 and dibenzo-18-crown 6;

DESCRIPTION OF THE PREFERRED EMBODIMENTS

Figure 1:
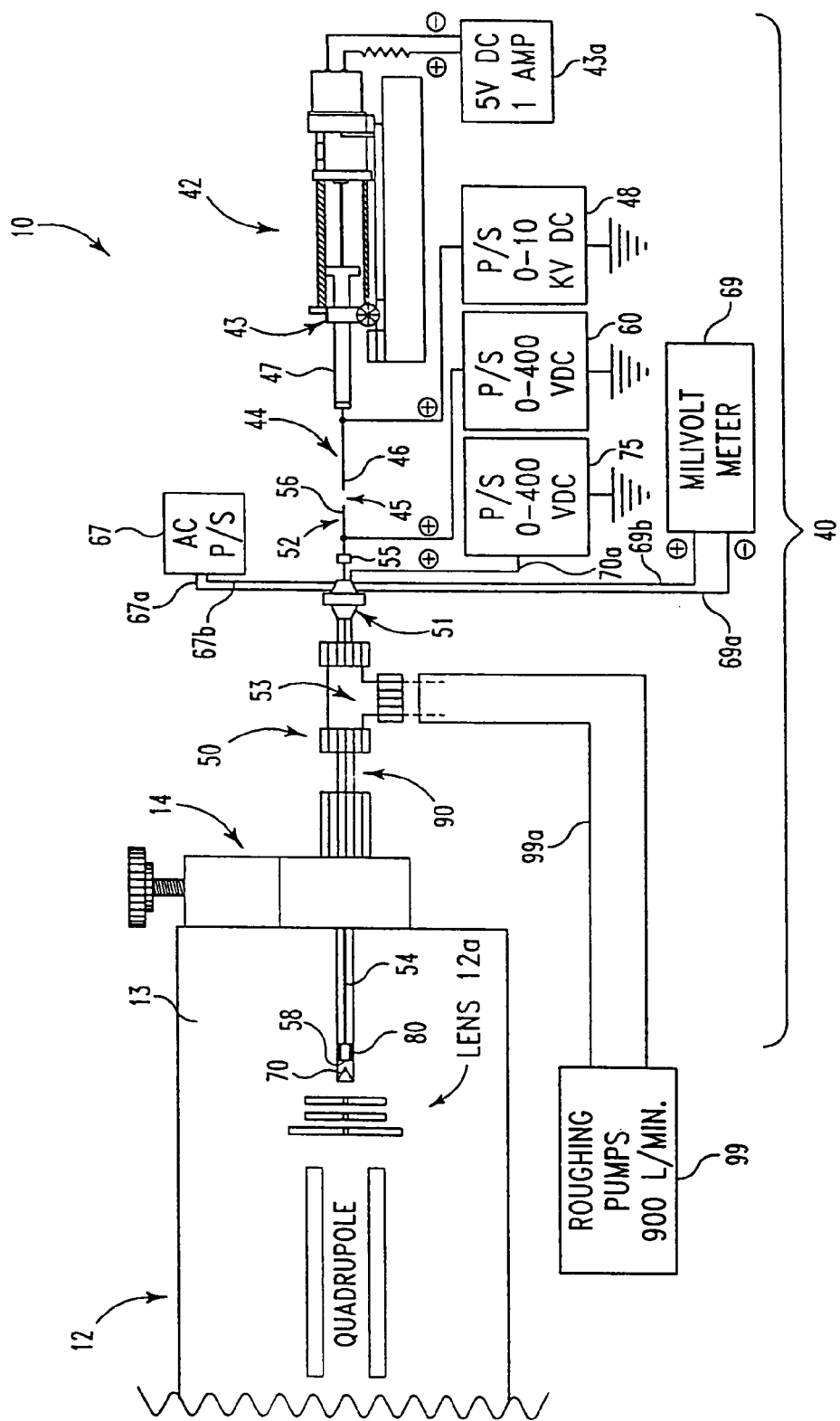
FIG. 1 is a schematic diagram of the mass spectrometric analysis system of this invention.

This invention comprises a novel method for characterizing the three-dimensional surface structure of molecules and molecular complexes, particularly proteins and small molecule-protein complexes, employing mass spectrometric analysis. As noted above, a novel electrospray ionization (ES) system, an ES probe interface and a method for introducing ionized molecules of interest directly into an unmodified electron ionization/chemical ionization (EI/CI) lens assembly of a mass analyzer, are the claimed subjects of U.S. Pat. No. 5,504,327, incorporated herein by reference. The ES source of the '327 patent is designed as a removable probe and is therefore conveniently referred to hereafter as an ES "probe."

The method of this invention of characterizing the three-dimensional structure of a macromolecule arises from the fact that the invention utilizes a non-natural composition of matter defined by a complex formed via the non-covalent binding of a small molecule to a protein. In the examples presented below, this involves various proteins, such as cytochrome c's, forming complexes with various crown ethers.

Moreover, this invention allows for the use of computational chemistry and molecular modeling methods to rationalize a protein molecular model that allows predictions to be made about the potential for binding of other small molecules to a protein molecule. In the method of this invention, the binding constants ($K_B$) of small molecules, such as crown ethers, to proteins are determined experimentally be ES-MS, and these experimentally determined constants are compared to the heats of formation ($\Delta H_f$) calculated using a general computational molecular model. The "heats of formation" are then converted to "heats of reaction" ($\Delta H_{RXN}$) via standard chemical equations. For the purposes of this disclosure, a "small molecule" is generally defined as a molecule having a molecular weight of less than about 1000 Daltons, molecules having a greater molecular weight being defined as "large molecules." The novelty and simplicity of the claimed method is based on the fact that ES-MS is the only experimental method which allows the generation of both individual gas-phase protein molecular ions and their complexes. This is important because the use of computational molecular models is greatly simplified when a gas-phase ion is utilized.

The invention particularly described and claimed herein is a method for characterizing the three dimensional structure of a protein molecule comprising: (a) mixing a small molecule with a protein so that the small molecule binds non-covalently to the protein to form a protein-small molecule complex; (b) performing electro spray ionization mass spectrometry ionization mass spectrometry to obtain the spectrum of the protein-small molecule complex; (c) using the spectrum from step (b) to calculate the binding constant(s) ($K_B$) for the binding of the small molecule or molecules to the protein; (d) repeating steps (a)–(c) with additional different small molecules; (e) calculating the heat of formation ($\Delta H_f$) for the binding of each of the small molecules used in steps (a)–(d) to a selected residue on the protein; (f) repeating step (e) for other selected residues on the protein; (g) comparing the binding constant (s) ($K_B$) calculated in steps (c) and (d) with the $\Delta H_f$ (or $\Delta H_{RXN}$ as required) values calculated in steps (e) and (f); and (h) utilizing the comparisons of step (g) to characterize the three-dimensional structure of the protein. This allows one to observe non-covalent complexes between small molecules and the surface of typically larger protein molecules, which have not, heretofore, been individually observable. More particularly, this technique may be used to study the binding of crown ethers to different types of cytochrome c protein complexes. Previous work by others had suggested the binding of certain crowns to the surface of proteins, such a cytochrome c, where the suggested binding site is the solvent-exposed protonated lysine residue.

FIG. 1 shows a system 10 for analyzing the mass spectra of molecules and molecular complexes of interest which is a subject of the allowed '688 application. Such a system 10 comprises a mass analyzer 12 having an inlet orifice means 14 for receiving therein ionized molecules of interest and molecular complexes to be analyzed and an electro spray ion source 40 connected to analyzer 12 for introducing ionized molecules of interest and molecular complexes therein for analysis. For convenience, when reference is made in this disclosure to include molecules and molecular complexes, such as, but not limited to, protein and crown either complexes.

The mass spectrometer shown in FIG. 1 is a schematic representative instrument and the discussion herein applies to mass spectrometers in a general sense. Inasmuch as such mass spectrometers are will known, complete details of its structure and operation need not be given here.

Electro spray ion source 40 can include a source 42 for providing a dilute solution of the molecules of interest, electro spray means 44 for generating a fine spray of tiny charged droplets of the solution, a high voltage means 48 for imposing first voltage on electro spray means 44, desolvation means 52 having an entrance orifice 56 positioned across a gap 45 from electro spray means 44 for receiving the charged droplets of solution and an exit orifice 58, a second voltage means 60 for imposing a voltage on desolvation means 52, means 67 and 69 for controllably heating desolvation means 52, sampling or skimmer means 70 for directing the ionized molecules of interest to the mass spectrometer 12, lens means 80 positioned upstream of skimmer means 70 for initially focusing the ionized molecules of interest after their exiting desolvation means 52 and prior to their entering skimmer means 70, an evacuable transparent dielectric encasing 90 for housing desolvation means 52, heating means 67 and 69, skimmer means 70 and lens means 80, and vacuum pump means 99 for creating a vacuum in encasing 90.

Mass analyzer 12 has a vacuum chamber 13 forming inlet orifice means 14, which forms a vacuum seal with evacuable encasing 90 adjacent the outlet side of skimmer means 70. Inlet orifice means 14 is of the conventional 0.50 inch (13 mm) vacuum lock type commonly found on conventional mass spectrometers, so details of its structure also need not be given here. Mass analyzer 12 can be defined by a single, double, triple or more quadrupole or any other type of mass spectrometer (e.g. magnetic sector/electric sector, QIT, ICR, FT-MS, etc.) Having an internal pressure of about $10^{-5}$ torr or less in its analyzer section.

The source 42 of the dilute solution can be provided by a syringe pump 43 coupled to a DC power source 43$a$ to pump the solution through a needle 46 to generate a fine spray of tiny droplets of the dilute solution in the gap area 45 adjacent the entrance of orifice 56 of capillary tube 54 which defines desolvation means 52. It is important to note that any other means of generating tiny charged droplets (e.g. ultrasound) of a sample may be introduced in the ES probe at 56. These droplets may be either positively or negatively charged, and may be of a very low flow rate, such as less than nanoliters per minute for example. The end or exit orifice or syringe needle 46 is preferably positioned about 0.5 to about 5.0 cm from entrance orifice 56. As an alternative to syringe pump 43, the dilute solution may be provided by a continuous infusion system (e.g., high pressure liquid chromatography pumps or self-sustaining electro spray). Voltage means 48 applies a high voltage to needle 46 in the range of about ±4000 VDC. Pump means 99 can include a conduit 99$a$ connected to a mechanical vacuum pump 99 with a capacity of about 900 L/min to create a vacuum in the evacuable encasing 90 in the range of about 10 torr to about $10^{-3}$ torr, preferably about 1 torr.

Referring now to FIG. 2, an isolated view of the ES probe 50 is shown in more detail wherein desolvation means 52 is defined by a capillary tube 54 having an upstream entrance orifice 56 and a downstream exit orifice 58. A voltage of zero to ±1000V is applied to tube 54 externally of dielectric encasement 90 by second voltage means 60 (FIG. 1). Capillary tube 54 preferably has an inner diameter of about 0.0625 inch, and an overall length of about 500 mm, preferably about 430 mm. Probe 50 has an overall length of about 44 cm. It is to be understood, however, that a capillary tube of any length may be employed.

The means for controllably heating capillary tube 54 can include an electrical resistance coil 66 wound about capillary 54 and a temperature sensor 68 operably connected to a readout means, definable by a voltmeter 69, via connectors 69$a$ and 69$b$ (FIG. 1) for correlating the voltage applied to the coil 66 with temperature. Electrical resistance coil 66 can include a coiled length of Nichrome wire with each end referenced as 67a and 67b coupled to an AC power source 67. In operation, coil 66 heats capillary tube 54 in the temperature range of about 25° C. to about 200° C.

Figure 4:
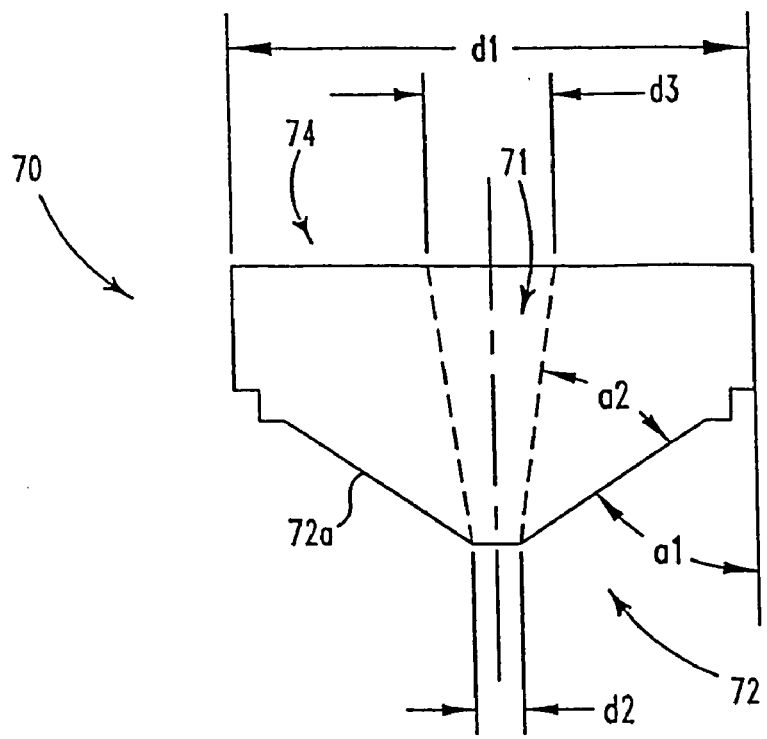
FIG. 4 is a cross section of the sampling cone or skimmer employed by the alternative embodiments of this invention as shown in FIGS. 1 and 2, respectively.
Figure 5:
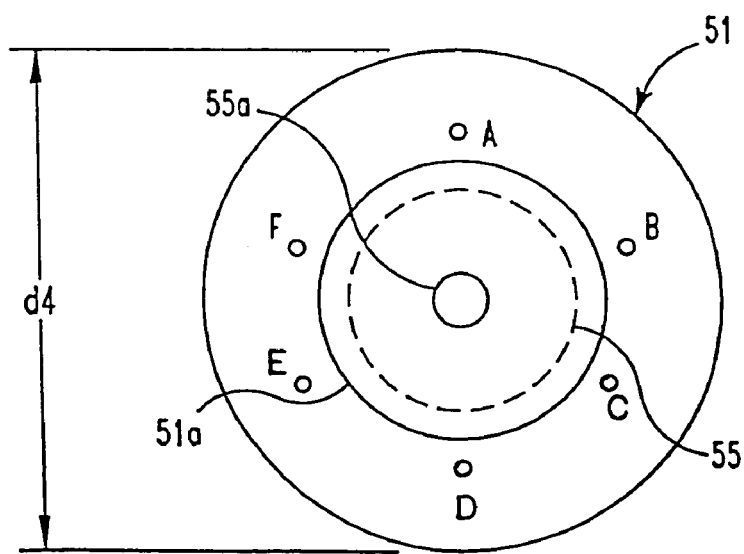
FIG. 5 is an end view taken from the left end of FIG. 2.

As shown in FIGS. 2 and 4, sampling cone 70 has an inlet side 72, and outlet side 74 and a central orifice 71 extending there through, with the inlet side 72 positioned at a first distance of about 1–10 mm. From the exit orifice 58 of capillary tube 54. Sampling cone 70 is preferably electrically isolated from tube 54 and has a separate voltage applied thereto by third voltage means 75 (FIG. 1) via connector 70a. Central orifice 71 has a frustoconical shape with a diameter $d_2$ at inlet side 72 of about 0.020 inch and a diameter $d_3$ at outlet side 74 of about 0.275-inch. Cone 70 has an outer diameter $d_3$ of about 0.50 inch (13 mm). Conical inlet side 72 is disposed at an angle $a_1$ of about 40° and the angle $a_2$ between the wall 72a of inlet side 72 and the interior wall of central orifice 71 is about 30°.

ES probe 50 can further include a vacuum endcap 51 disposed in evacuable encasement 90 adjacent entrance orifice 56 of capillary tube 54. Endcap 51 can be provided with a plurality of holes for feeding electrical connectors through to the interior of housing 90. In a preferred embodiment, endcap 51 has an outer diameter $d_4$ of about 0.75 inch and is provided with (6) wire feedthrough holes A–F, where two of the holes carry wires 67a and 67b to form heating coil 66 coupled to power source 67, two more of the holes carry wires 69a and 69b coupling the temperature sensor 68 to voltmeter 69, a fifth hole carries wire sensor 68 to voltmeter 69, a fifth hole carries wire 70a coupling sampling cone 70 with voltage means 75, and a sixth hole could carry a wire providing separate voltage to the spacer lens 80.

Fitting 55 further allows for the selective positioning of the exit orifice 58 of tube 54 relative to the inlet side 72 of sampling cone 70. Fitting 55, provided with a central bore 55a, acts as a compression clamp when a finger-tight (Knurl-Lok) fitting 55 is tightened in central opening 51a of endcap 51 to maintain the vacuum within encasing 90 while fixing in location capillary tube \54 relative to encap 51. To selectively position tube 54, fitting 55 may be loosened and tube 54 pushed or pulled slightly to alter the distance between exit and orifice 58 and skimmer inlet side 72. Additionally, tube 54 may be selectively threaded into spacer lens 80 to achieve similar results. During the operation of probe 50, fitting 55 cannot be loosened, of course, so either the syringe pump 43 may be moved closer to or farther from capillary entrance orifice 56 to alter gap 45, and/or the probe 50 itself may be moved to alter the gap 45 and/or the distance between the skimmer outlet side 74 and the lens stack 12a of spectrometer 12.

Evacuable dielectric housing 90 is constructed preferably of glass having an inner diameter of about 0.510 inch. While glass is preferable, other dielectric materials may prove suitable for housing 90.

Lens means 80 can include a metal or other conductive spacer adapted to be positioned upstream of the inlet side 72 of sampling cone 70 for initially focusing the ions of interest after their exit from the exit orifice 58 of capillary tube 54 and prior to their entering the orifice 71 of sampling cone 70. In a preferred embodiment, brass spacer lens 80 is not insulated from but is threadably affixed to capillary tube 54 adjacent its exit orifice 58 so that the inner (downstream) face of spacer lens 80 can be generally flush with orifice 58. Being threadable, spacer lens 80 is adjustable to selectively position the downstream side of spacer lens 80 in relation to the inlet side 72 of sampling cone 70.

As shown in FIG. 3, spacer lens 80 is provided with a central threaded orifice 82 and a plurality of longitudinal voids 84 extending there through all about its circumference. Voids 84 allow for the solvent molecules and any impurities, and molecules having improper kinetic energy, to be drawn there through and removed from within housing 90. Spacer lens 80 can be electrically isolated from the capillary tube 54 but, as indicated above, it need not be. In the event spacer lens 80 is electrically isolated from tube 54, probe assembly 50 can further include means for applying a separate voltage to spacer lens 80. Spacer lens 80 also acts to support capillary tube 54 concentrically within the encasement 90 by its peripheral surfaces 81 engaging the interior wall of encasing 90 to secure and maintain the coaxial alignment of the exit orifice 58 of tube 54 with the central orifice 71 of sample cone 70 and the lens stack 12a of mass spectrometer 12.

The ES probe utilizes the heated capillary for desolvation and features the skimmer cone and the threaded capillary tube resting in a threaded spacer. This design allows for each and reproducible adjustment between the tube and skimmer. Al ES probe components are concentric with the lens stack and quadrupole analyzer. The positioning of the probe may follow either of two patterns: just in front of the removable ion volume cavity in an EI/CI lens assembly; or approximately 0.5–3.0 cm from the first lens in the lens stack 12a.

The ability to switch between EI/CI and ES by simply removing the ion volume and inserting the ES probe (10–15 minutes), without physically reconfiguring the instrument, adds greatly to the versatility of this invention. The 13-mm probe diameter facilitates the use of ES experiments on any instrument with a 13-mm (or one-half inch) vacuum lock coaxial to the lens assembly. The ES probe can accommodate any lens stack arrangement coaxial to the mass analyzer. The size of the probe, the convenience of its use, the ready availability of its components, the ease of adjustment if its dimensions, its demonstrated high ion currents with or without modification of the remaining structure of the source, and the ease with which it can be maintained and modified, each contribute to the enhanced utility of the invention.

This invention thus provides an economical ES source designed as a probe capable of insertion into a source designed as a probe capable of insertion into a standard 13-mm (one-half inch) vacuum lock that has been shown to produce the same spectra as those produced with other much more expensive and complex electro spray sources. The probe construction of assembled components in a glass tube reduces the volume so that a 13-mm vacuum lock of conventional mass spectrometers may be accommodated. The demonstrated ability to use this ES probe with a standard configuration EI/CI lens assembly has obvious advantages.

Further provided is a method for introducing desolvated ionized molecules and molecular complexes of interest into a mass spectrometer 12 for analysis, including the steps creating a dilute solution of molecules of interest in a solvent, generating a fine spray of tiny droplets of the dilute solution of molecules of interest and solvent with an electro spray means 46, charging the tiny droplets of the dilute solution with a high voltage means 48, providing a desolvation tube 54 having an entrance orifice 56 and an exit orifice 58, positioning the entrance orifice 56 of desolvation tube 54 adjacent the point of generation of the fine spray of tiny droplets at syringe needle 46, applying a voltage to desolvation tube 54 by a voltage means 60, receiving the charged droplets in the entrance orifice 56 of desolvation tube 54, transporting the droplets to the exit orifice 58 of desolvation tube 54 employing a heater coil 66 coupled to a temperature sensor 68 to substantially desolvate the droplets during their transport through tube 54 to provide ionized molecules of interest at the exit orifice 58 of tube 54, focusing the ionized molecules if interest after their exiting of the desolvation tube 54, and directing the focused ionized molecules of interest upon their exit from the focusing means 80 through a sampling cone 70 having a voltage applied thereto, whereby the voltage differential between desolvation tube 54 and the sampling cone 70 acts to select ions with proper kinetic energy and electrostatically focuses the ions to be transported to the mass analyzer 12.

Sampling cone 70, because of its shape and voltage differential with desolvation or capillary tube 54, serves as a type of filter allowing only ions of the proper kinetic energy to pass through its central orifice 71 on to the mass analyzer 12. Ions with higher kinetic energy generally have a greater tendency to move in a substantially linear fashion and, therefore, a greater tendency to travel through the central orifice 71 of cone 70. Those ions with insufficient kinetic energy are deflected by conical wall 72a of the inlet side 72 of cone 70 and eventually withdrawn via vacuum back upstream through longitudinal voids 84 provided in spacer lens 80.

The method for characterizing the three dimensional structure of a protein complex can further include creating a solution of different interacting molecules comprising small molecules and larger protein molecules, adding a predetermined amount of crown ethers to the solution so that the smaller crown ether molecules bind to the larger protein molecules, charging the sample solution, generating a fine spray of tiny droplets of the solution with an electro spray means 46 and a first voltage means 48, positioning the entrance orifice 56 of a desolvation or capillary tube 54 adjacent the point of generation of the fine spray of tiny droplets adjacent a syringe needle 46, applying a second voltage to capillary tube 54 with a second voltage means 60, drawing and receiving the charged droplets in the entrance orifice 56 of tube 54, transporting the droplets to the exit orifice 58 of desolvation tube 54, controllably heat in desolvation tube 54 substantially desolvate the droplets during their transport through tube 54 to provide ionized protein molecule complexes at the exit orifice 58 of tube 54, focusing the ionized protein molecule complexes after their exiting the desolvation tube 54 with a focusing lens means 80 positioned upstream of a sampling cone 70 and directing the focused ionized protein molecule complexes upon their exit from the focusing means 80 through sampling cone 70 to remove inadequately ionized molecule complexes and on through to mass analyzer 12. This allows one to observe non-covalent complexes between small molecules and typically larger protein molecules, which have not, heretofore, been observable. Specifically, this technique may be used to study the binding of crown ethers to different types of cytochrome c protein complexes, which may be generalized to all protein/small molecule non-covalent interactions. Previous work by others has suggested the binding of certain crowns to the surface of proteins, such as cytochrome c where the suggested binding site is the solvent-exposed protonated lysine residue.

In the setup of system 10 provided by this invention and utilized in the experiments discussed below, the syringe pump 43 emitting the fine spray aerosol was positioned collinearly with and about 0.5 cm away from the capillary tube 54. The right portion of the probe 50 (30–35 cm) was then inserted through the front gate valve (inlet orifice means 14) of the mass spectrometer 12, which in other experiments is used to insert an ion volume. Any means of generating an electro spray aerosol of a sample will work with this ES probe. In this instance, the aerosol originates from the blunt needle 46 (Hamilton 80426, 25 gauge, #3 point) fitted to Hamilton #701 (Reno Nev.) 10 µL syringe 47 using a flow rate of 2 µL/min of $3–7\times10^{-5}$ M solution. Syringe needle 46 was maintained at a potential of about 4000 VDC by first voltage means 48. Capillary tube 54 was a stainless steel tube (Upchurch Scientific, Oak Harbor, Wash.) maintained at a potential of about 170 VDC by second voltage means 60. As noted above, tube 54 need not be constructed of metal and may be made from other suitable electrically conductive materials. One end (exit end 58) of the capillary tube 54 is threaded into the spacer lens 80 until the inner (downstream) face of the spacer is, typically, flush with orifice 58. The inner surface of the spacer lens 80 is positioned about 3 mm from the inlet side 72 of skimmer cone 70. The ES probe 50 is evacuated through the 13-mm encasement 90 by means of a stainless steel Cajon Ultra-Torr Tee 53 (½, SS-8-UT-3, Cajon Company, Macedonia, Ohio) and connecting pump conduit 99a leading to pump 99. A pumping capacity of 834 L/min (2 Edwards 18's @ 417 L/min each) has been found by the applicants to be adequate for efficient operation.

External electrical connections at the probe 50 provided for application of about 170 VDC on the capillary tube 54, about 58 VDC on the skimmer cone 70, and the heating of the capillary tube 54 to about 95° C. using an alternating current power source 67 (Variac, typically 10 VAC). The high voltage, capillary, and skimmer voltages are referenced to and use a common ground and are isolated from the grounded instrument to reduce interference from occasional high voltage arcing.

The heating coil 66 is preferably made from 0.5-mm diameter Nichrome wire (Omega Engineering, Stamford, Conn., N180-020-50, AWG 24) wound around the capillary tube 54 insulated, as are all internal probe wires, with fiberglass sleeving (Omega Engineering, FBGS-S-24). An iron-Constantan thermocouple 68 (Scientific Instrument Services, Ringoes, N.J., TH-4) can be used for temperature measurement operably connected with a Keithley 150B microbolt meter 69 via connectors 69a and 69b. The high voltage was provided by Antek (Palo Alto, Calif.) PS-4 series power supply (first voltage means 48) used by Extrel for the FAB accessory. Two identical Heathkit (Benton Harbor, Mich.) IP-17 regulated power supplies can provide the two other DC voltages (second and third voltage means 60 and 75). The power supply voltages can be monitored with Simpson 260 (analog) and 460 (digital) millimeters.

The probe endcap 51 with wire feedthrough holes A–F can be sealed to the housing 90 by using Apiezon W (Apiezon Products, Ltd, England) vacuum was. Skimmer cone 70 can be sealed to the housing 90 by using DEVCON 5-Minute epoxy (DEVCON CORP., Danvers, Mass.). The encap 51 was constructed of stainless steel and machined to desired dimensions. Fingertight fitting 55 was provided by a stainless-steel Knurl-Lok I fitting with a PEEK ferrule (Alltech Associates, Inc., Deerfield, Ill.) for carrying the capillary tube 54 machined to desired dimensions and pressed into the endcap 51 to support tube 54 coaxially within a central bore 51a formed in endcap 51.

The pressure in the line 99a leading from the mechanical pumps 99 to the probe tee 53, which can be measured using a Hastings gauge, is preferably about 1 torr. The pressure in the source and analyzer manifolds can be monitored by using ion gauge tubes giving typical values, respectively, of about 1.5×10$^{-6}$ torr. The capillary-to-skimmer gap may be adjusted to maintain pressure in the analyzer section of the mass spectrometer at about 10$^{-6}$ torr.

EXAMPLE ONE

At least three kinds of quadrupole mass spectrometers have been used with this invention to characterize the ES probe: two single quadrupoles and one custom, double quadrupole instrument. However, any type of mass spectrometer system could accommodate this ES probe interface.

Figure 6:
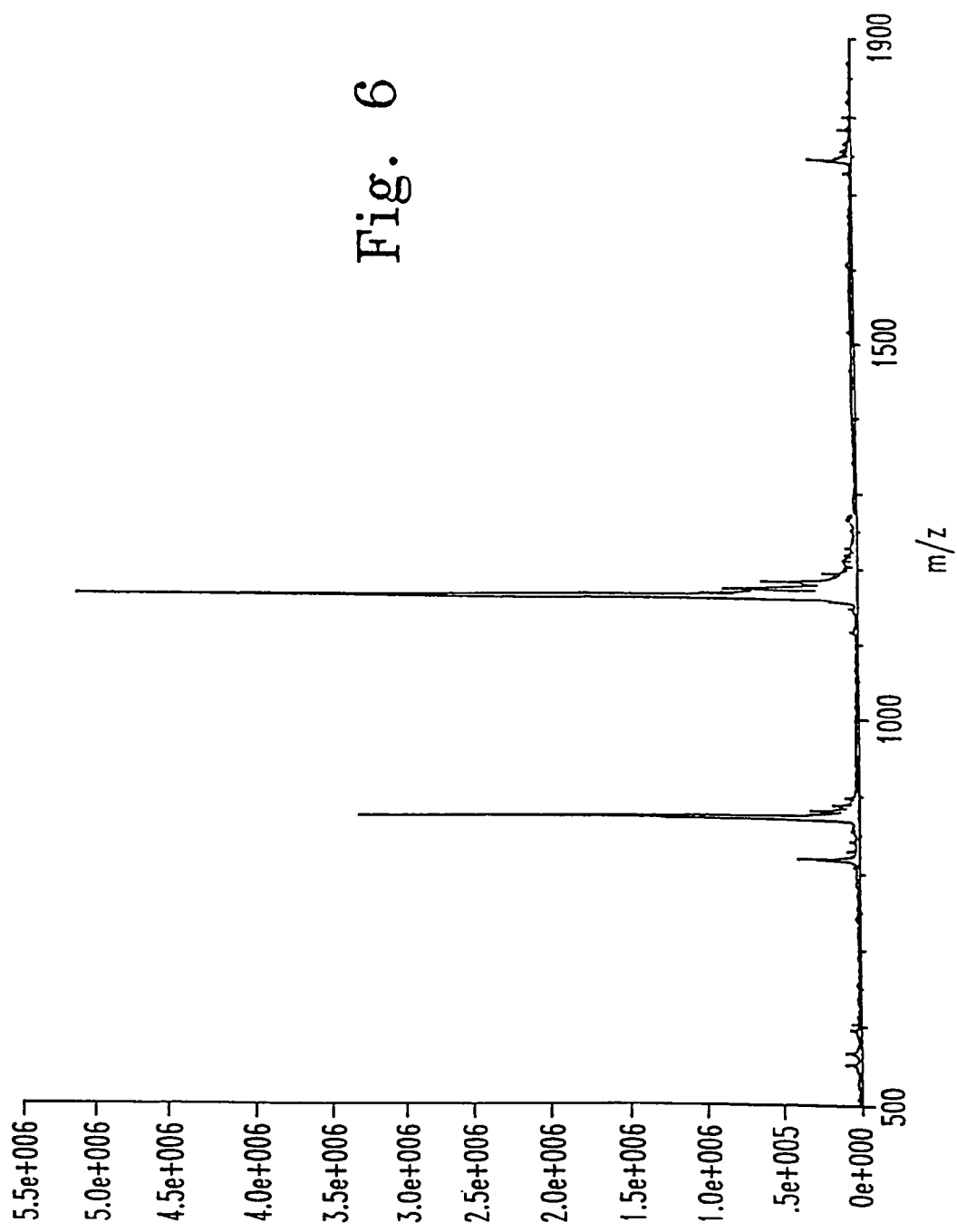
FIG. 6 is an electrospray ionization mass spectrum of glucagon.

In this experiment, the following polypeptides were used to optimize the ES probe of this invention: angiotensin III (Sigma #A-0903, 30 pmol/μL, bradykinin (Sigma #B-3259, 47 pmol/μL), renin substrate (Sigma #R-8380, 56 pmol/μL, melittin (Sigma #M-2272, 50 pmol/μL), and glucagon (FIG. 6, Sigma #G-1774, 50 pmol/μL). These polypeptides were prepared with equal parts of methanol and 1% acetic acid/water. Cytochrome c (FIG. 7, horse heart, Sigma #C-2506, 67 pmol/μL) was prepared with 2% acetic acid/water and methanol.

Figure 7:
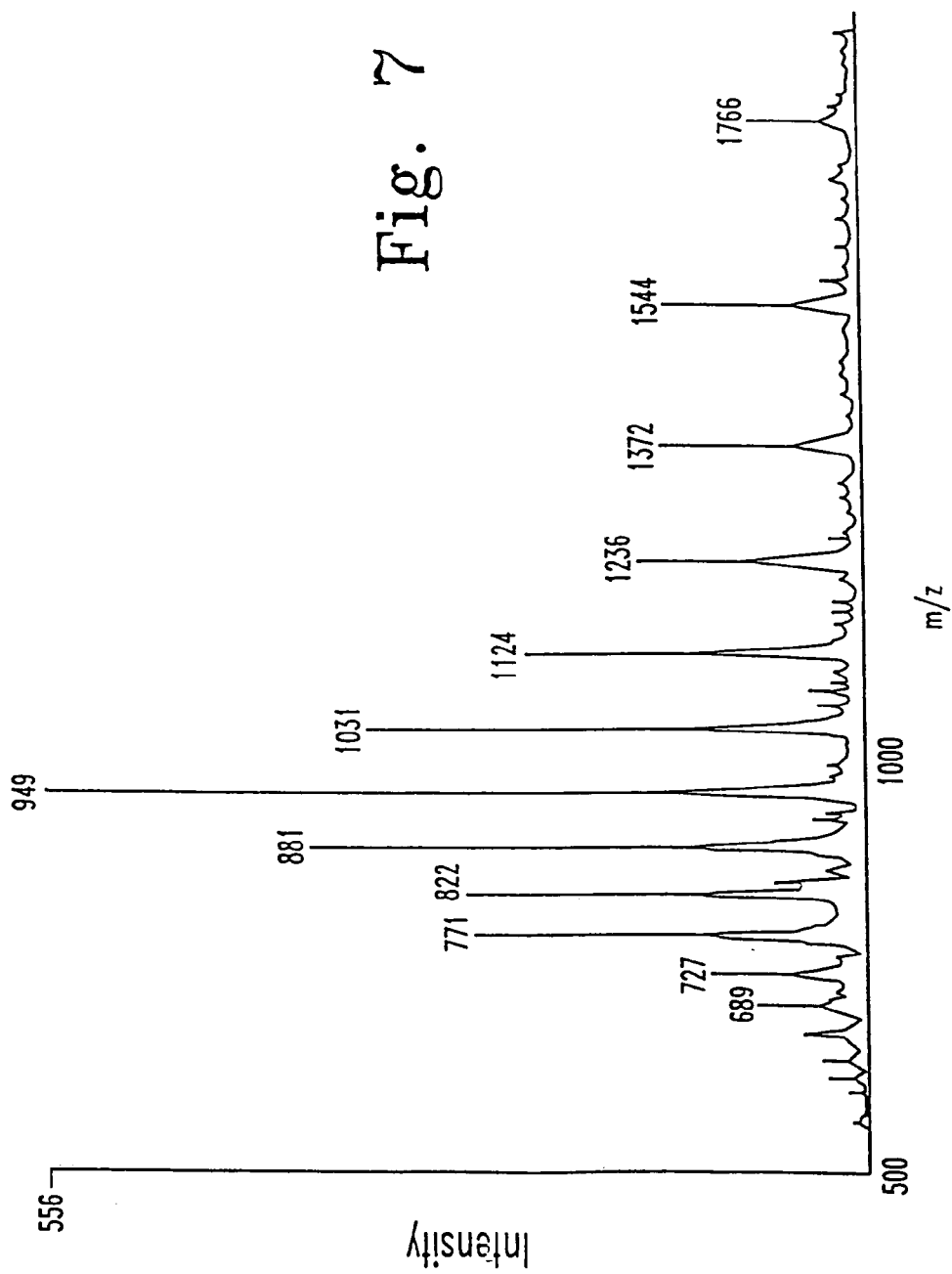
FIG. 7 is an electrospray ionization mass spectrum of cytochrome c (horse heart)

The ES spectrum of glucagon depicted in FIG. 6 was characterized using a standard EI/CI lens assembly on an Extrel dual quadrupole mass spectrometer (50 in 50:50 MeOH:H$_2$O, 1% acetic acid infused at 2 μL/min). The spectrum was acquired with a Taknivent (Maryland Heights, Mo.) Vector Two data system scanning at 72 u/s, between a mass range of 500 to 1900 u over a 6.60 minute period with the electron multiplier set at −1800 VDC. In FIG. 7, the ES spectrum of cytochrome c (horse heart) was characterized using an Extrel ELQ 400 single quadrupole mass spectrometer (67 pmol/μL in 50:50 MeOH:H$_2$O, 2% acetic acid infused at a 2 μL/min). The spectrum was acquired with an Extrel/Sun Ionstation data system scanning at 333 u/s between a mass range of 450 to 2000 u over a 1.88 minute period with an electron multiplier set at −1800 VDC.

The data collected on the three different instruments gave similar results which were quite comparable with previously published results. While no attempt was made to maximize the sensitivity of the system, as little as 8 seconds of accumulated scans, at 400 u/s covering a mass range of 1550 u, was found to produce a characteristic spectrum. In the spectra of glucagon and cytochrome c shown in FIGS. 6 and 7, respectively, the relative intensity differences within the envelop of peaks as compared to other published data may be attributed to different concentration of acid or to slight differences in operating conditions. The change in acid concentration causes a shift of the multiply protonated molecular ion envelope, increased acid concentration showing more highly protonated species. Glucagon (FIG. 6, 3483 Da) was characterized by two predominant peaks, the +4 (m/z 872) and the +3 (m/z 1162) multiply protonated molecular ions. This is representative of other reported spectra (the small peaks were not identified). Cytochrome c (12,360 Da was characterized (FIG. 7) by an envelope of ions representing a range of charge states from 7 to 20 with the most intense peak at +13 (m/z 949). The spectrum compare favorably with the envelope of peaks previously reported. Comparisons were obtained on both single and dual quadrupole instruments, with few differences seen inspectra or total ion count.

EXAMPLE TWO

A study was conducted of the non-covalent interactions of three crown ethers, dicyclohexano-18-crown-6 (#1), 18-crown-6 (#2), and dibenzo-18-crown-6 (#3) (FIGS. 17A–17C) with three types of cytochrome c; horse tuna and yeast, utilizing the ES probe 50 and method of this invention. Each of the three different types of cytochrom c displayed different degrees of binding for each of the three crown ethers; however, the binding of the crown ethers was found to increase in the order given above with dicyclohexano-18-crown-6 binding the most tightly and dibenzo-18-crown-6 binding the least tightly.

More particularly, the experiments showing binding of crowns to cytochrome c were done by adding 1, 2, and 3 mol ratios to a 70 pmol/μL mixture of the three different cytochrome c's. The solutions were prepared with equal parts of methanol/water with 1% acetic acid. Typical sample conditions were, 95° C., 2 μL/min, 4000 VDC on the syringe, 170 VDC on the capillary tube, and 60 VDC on the skimmer.

Figure 8:
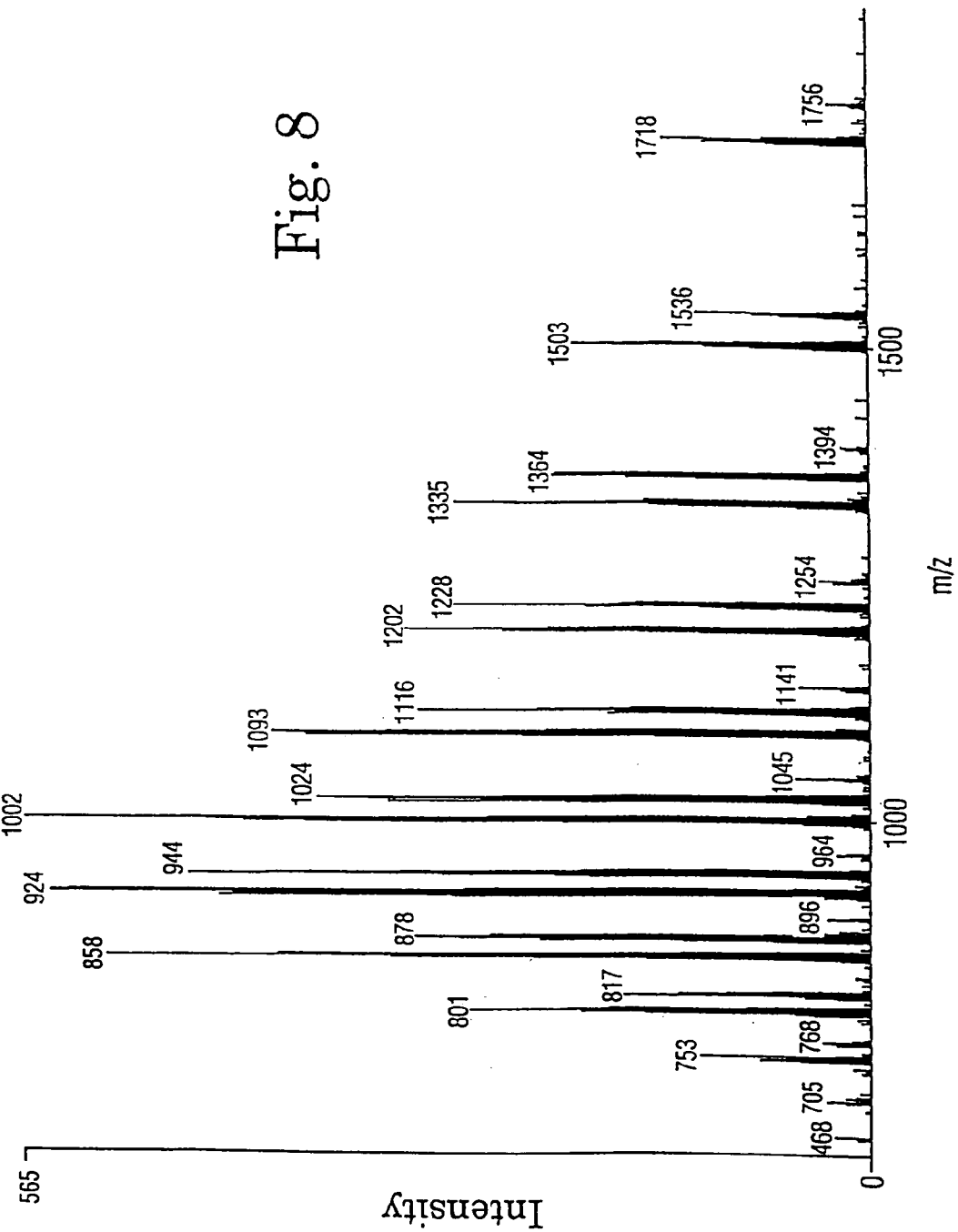
FIG. 8 is an electrospray ionization mass spectrum of cytochrome c (tuna heart) with 1B-Crown-6 in a 1:1 mol ratio.
Figure 9:
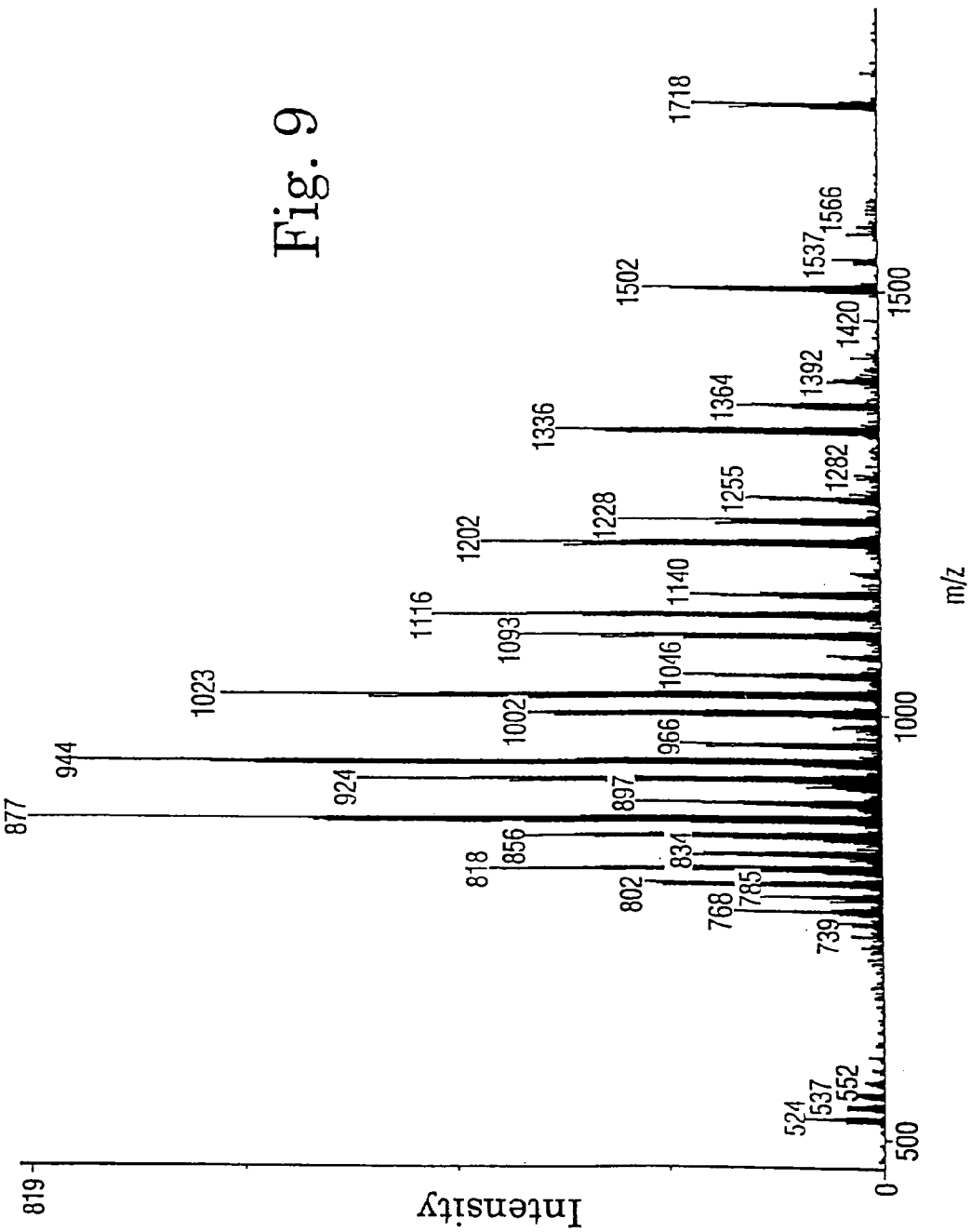
FIGS. 9–11 are electrospray ionization mass spectra of cytochrome c complexed with three different crown ethers.
Figure 10:
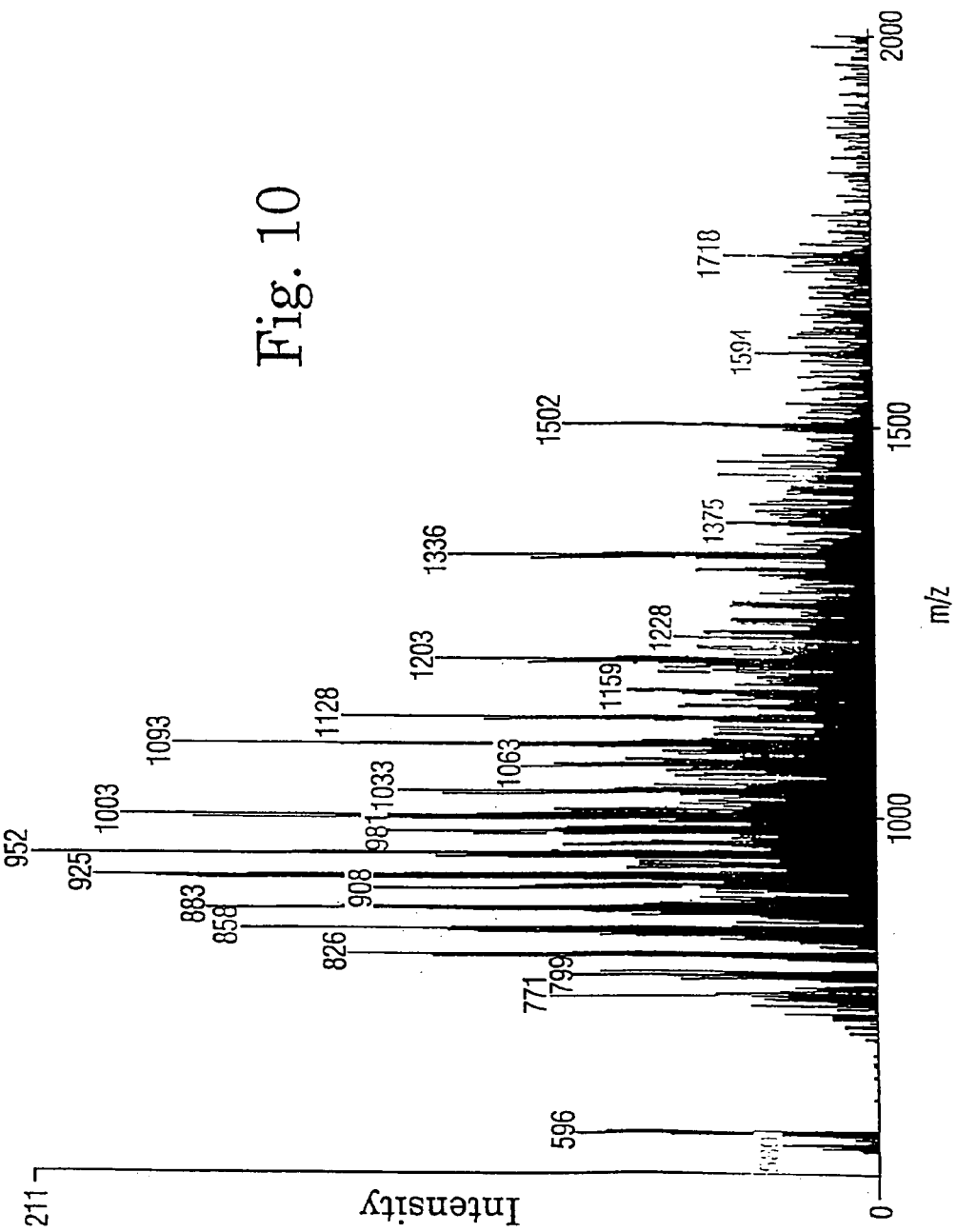
Figure 11:
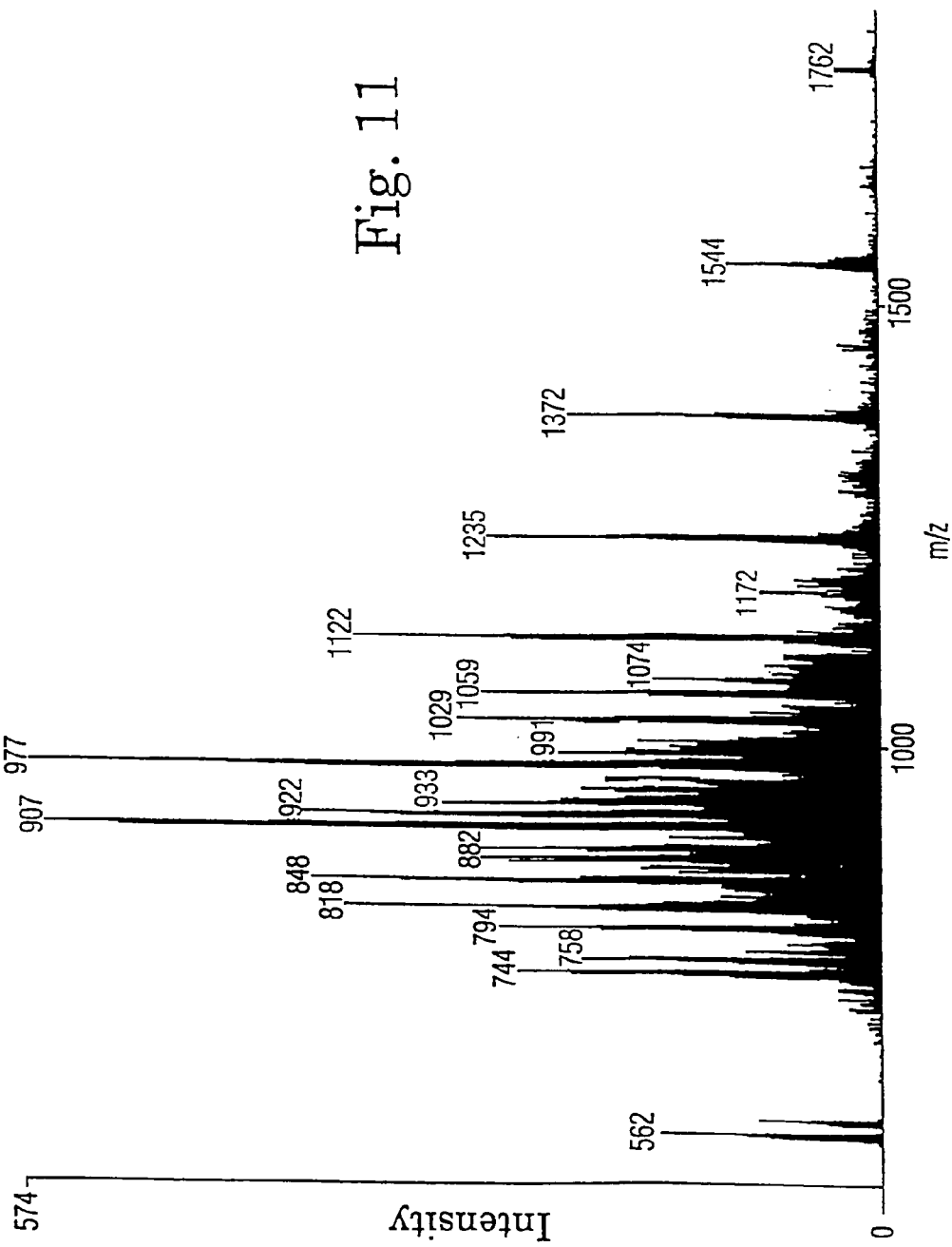
Figure 12:
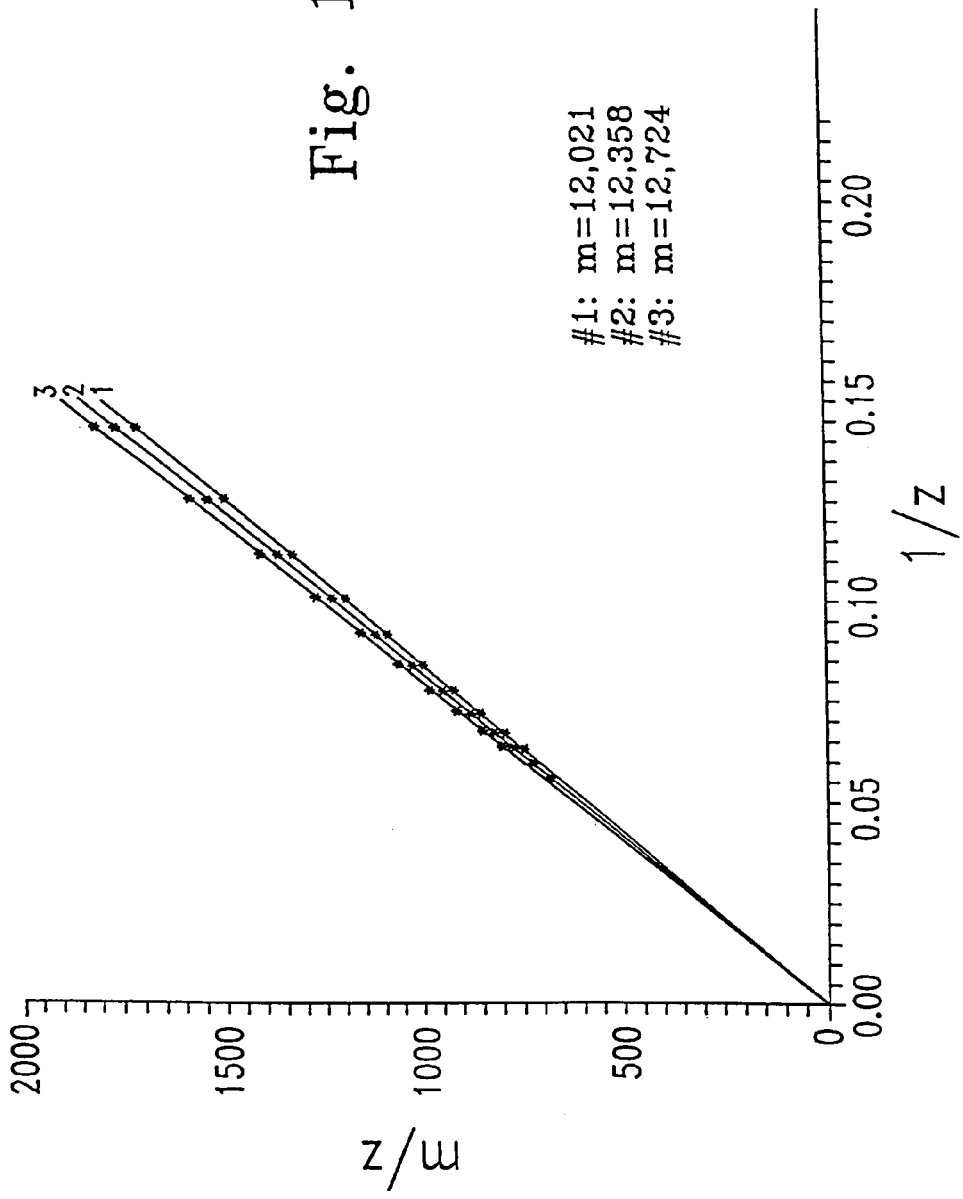
FIGS. 12 and 13 are graphical presentations of the molecular weights of different cytochrome c's (FIG. 12) and cytochrome c complexes (FIG. 13) determined from linear plots of each of the proteins set of characteristic m/z peaks vs. l/z.
Figure 13:
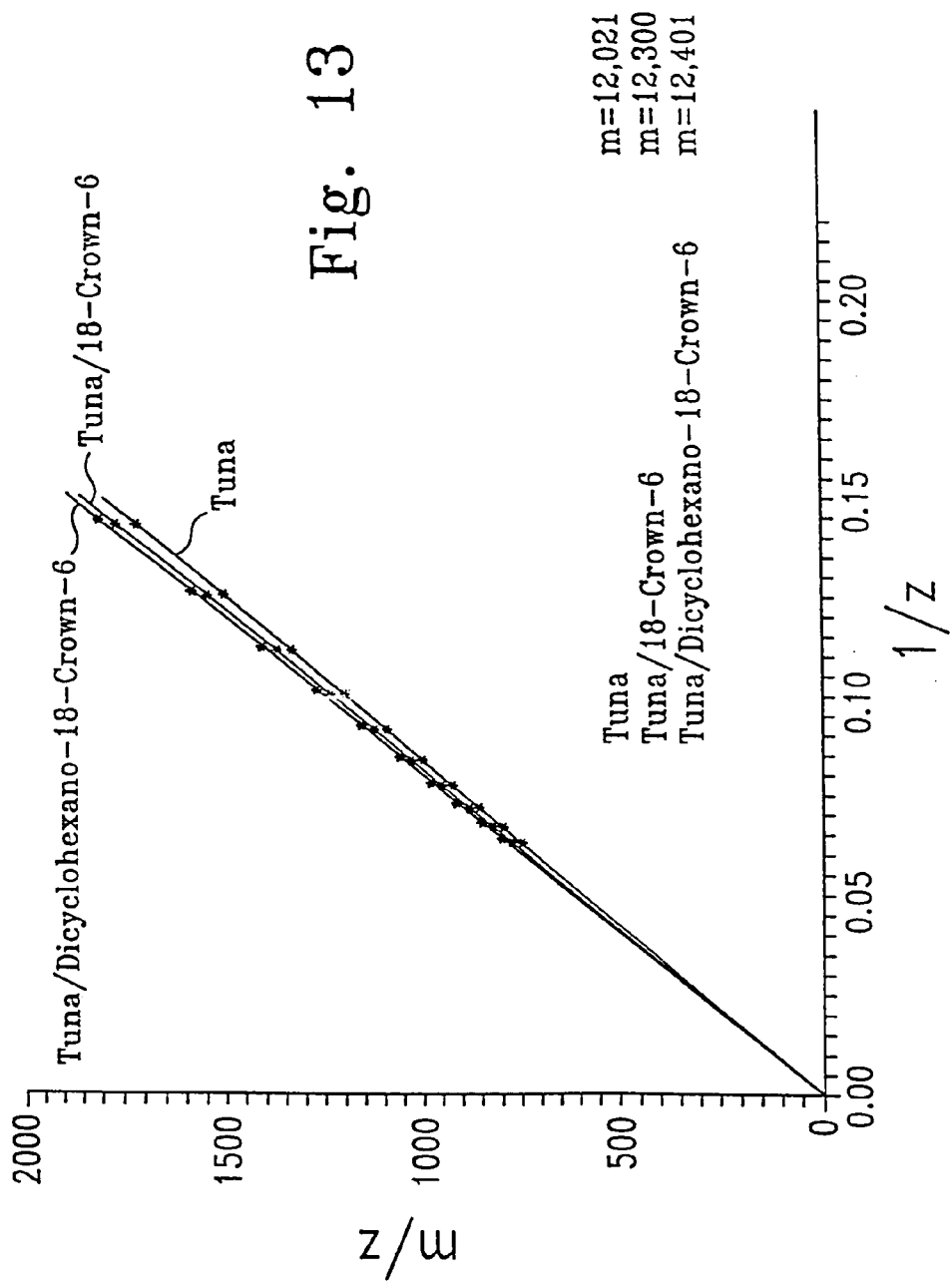
Figure 14A:
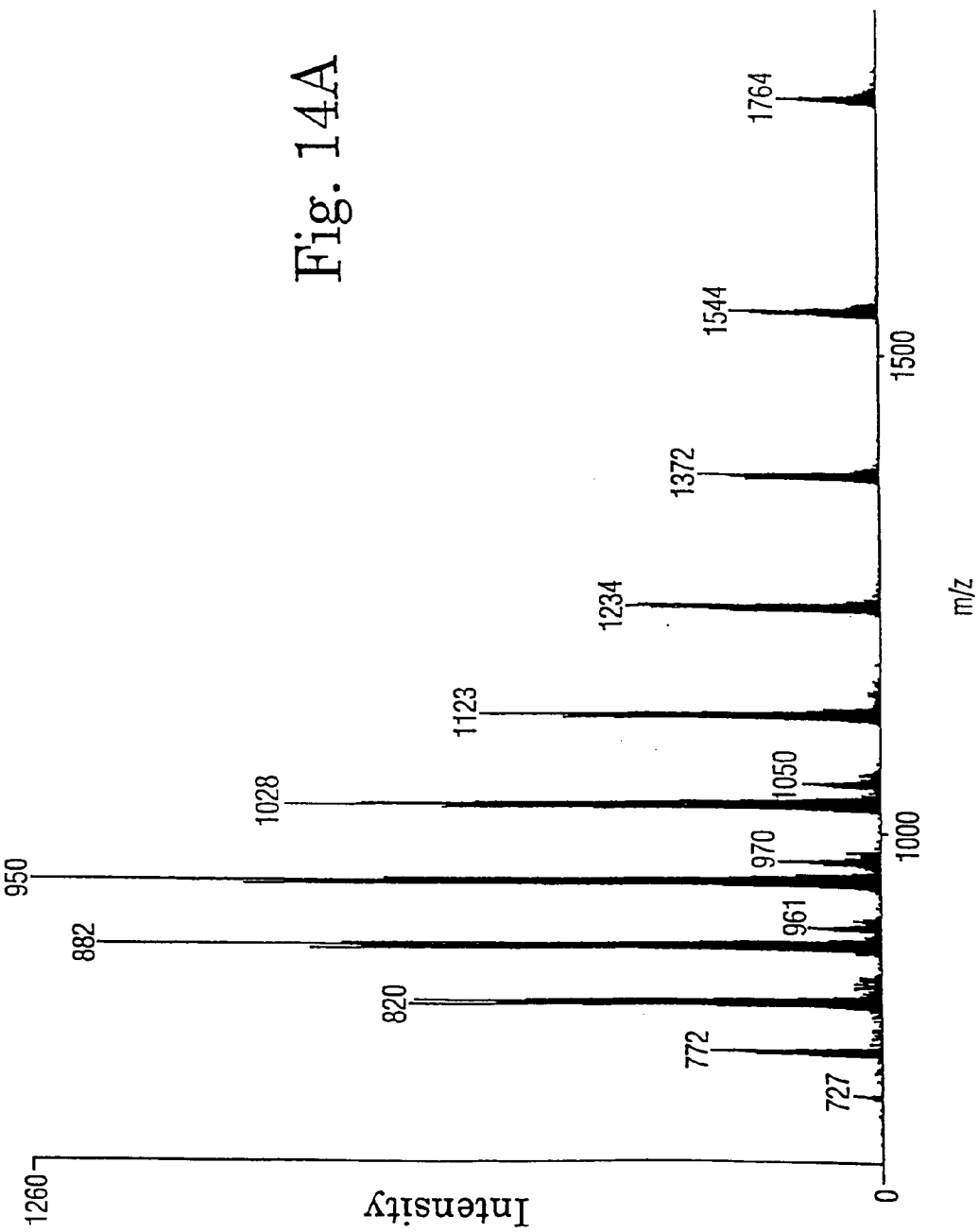
FIGS. 14–16 are electrospray ionization mass spectra of horse heart cytochrome c complexed with three different crown ethers.
Figure 14B:
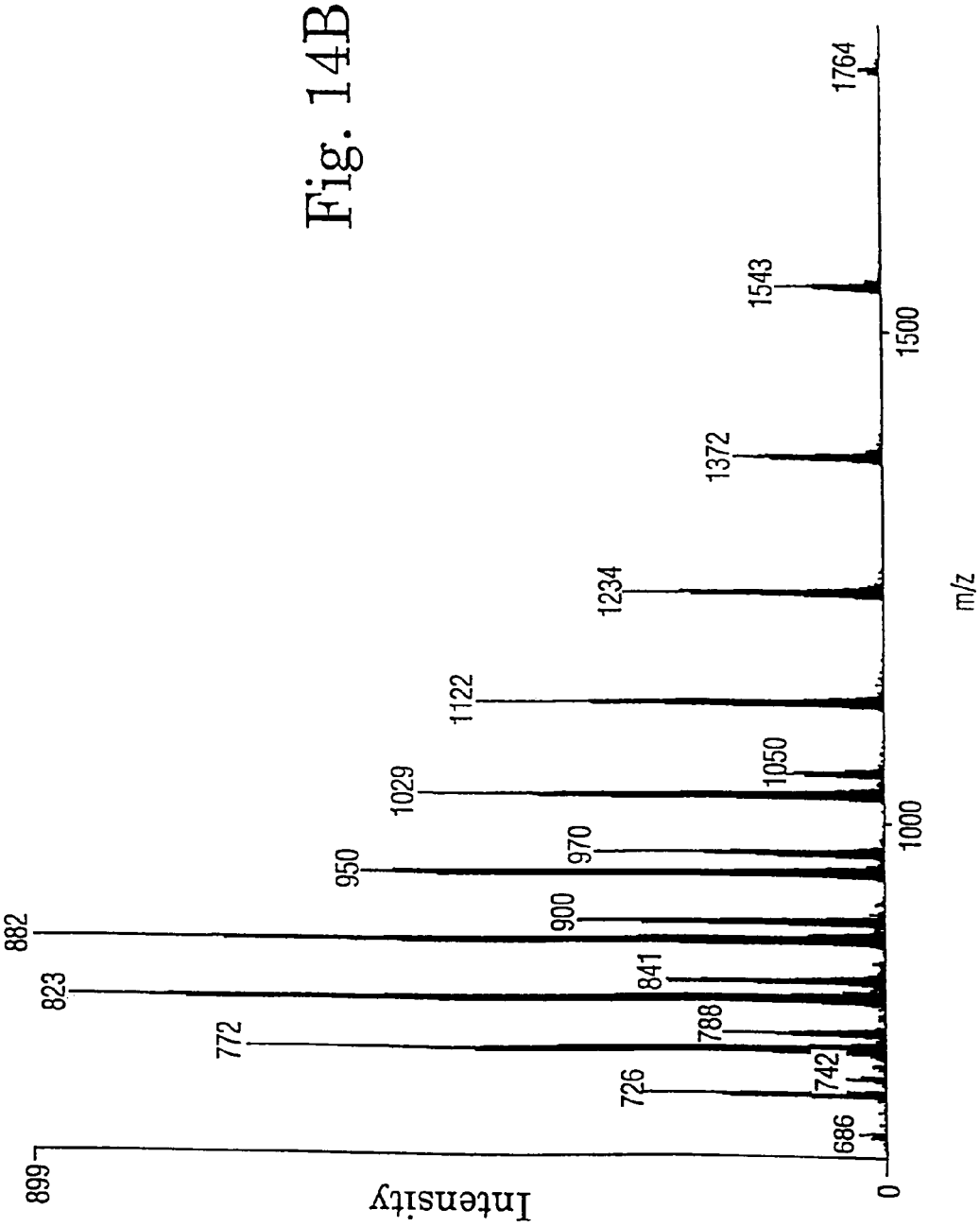
Figure 15:
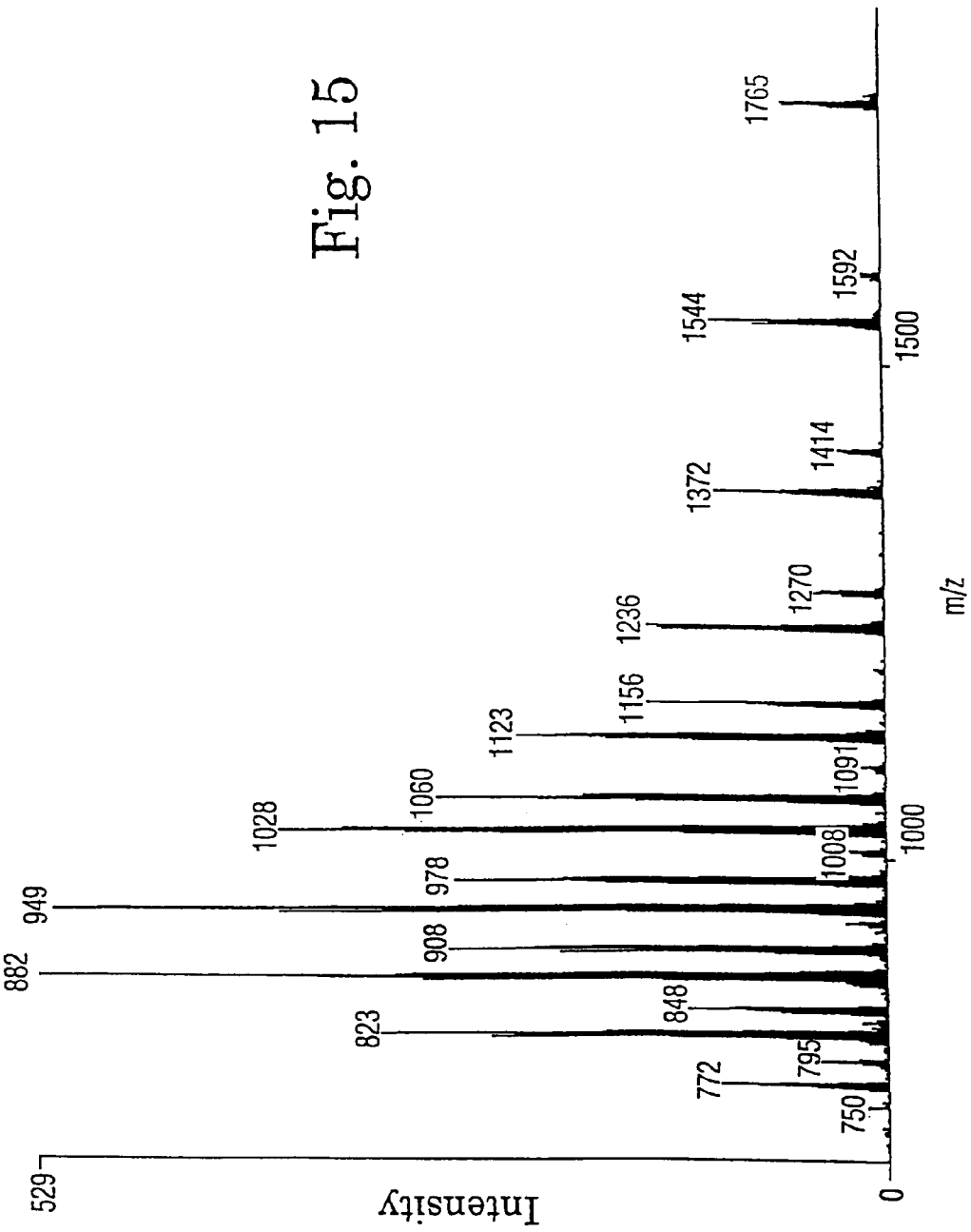
Figure 16:
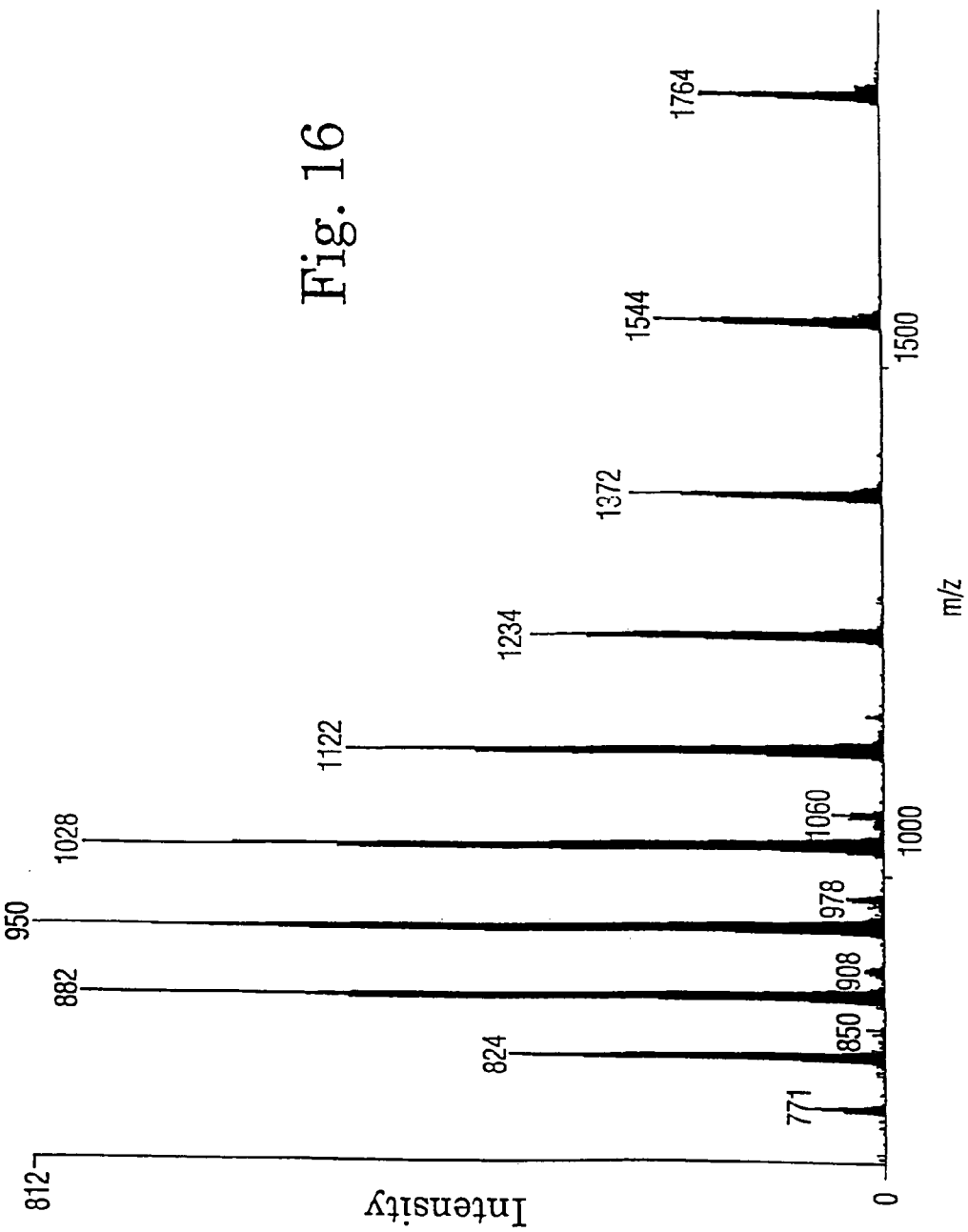

The binding of crowns (shown for Tuna Heart in FIG. 8 and for Horse Heart in FIGS. 14–16) increases with increasing concentration. FIGS. 14A and 14B expressly show the increase in crown binding to Horse Heart that occurred when the concentration was increased for a 1:1 mol ration to 1:2. An excess of crown produces a spectra showing a pronounced set of peaks corresponding to a protein/protein-crown complex, which in addition exhibits a new species with a greater number of charges (shown for Tuna Heart in FIGS. 9 and 10 and for Horse heart in FIG. 11). This bimodal distribution may be representative of a conformational change in the protein. The molecular weights of the cytochromes were determined from linear plots of each of the proteins set of characteristic m/z peaks vs. l/z (FIG. 12), where the slope of the line gives the experimental molecular weight. These values were in close agreement to previously published molecular weights. Similar plots were made to determine the molecular weight of the protein/crown complexes (FIG. 13 shows a plot of two different bound crowns compared to the protein alone).

Signals representing the complex resulting from non-covalent binding of crown ethers to cytochrome c are observed in the ES mass spectra. Because the crown ethers do not change the proteins charge, the characteristic charge envelope remains. The increase in mass of the complex is seen as an intercalated envelope of a slightly higher m/z. The linear plots of m/z vs. 1/z (FIGS. 12 and 13) passing through the origin have proven to be a simple method for finding the molecular weight of the proteins and protein complexes, as well as providing a test for correct charge assignment. The suggested conformational change of the protein with increasing crown concentration is an interesting result and may be due to an increase of the surface hydrophobicity as suggested by recent work using other approaches.

In this example, the K values for the first mole of crown ether binding were determined from the mass spectra ion counts using the following equation:

$$K_{B1} = \frac{\sum_{z=1}^{z=n} (PL_z)}{\left(\sum_{z=1}^{z=n} (P_z)\right)\left([\text{Ligand}] - [\text{Protein}]\frac{(PL_z)}{\sum_{z=1}^{z=n} (P_z)}\right)}$$

Where:

$$\sum_{z=1}^{z=n} (PL_z) = \text{the sum of the Protein-}$$

Ligand molecular ion ES/MS peak heights of charge z.

$$\sum_{z=1}^{z=n} (P_z) = \text{the sum of the free}$$

protein molecular ion peak heights of charge z.

[Ligand]
  =the Molar concentration of the ligand (e.g., crown ether) in the sample solution.
[Protein]
  =the Molar concentration of protein in the sample solution.

The average calculated $K_B$ values for each of the three crowns bound to the tuna cytochrome c are presented below in Table 1:

TABLE 1

Calculated $K_B$'S ($M^{-1}$) From ES-MS Data
Cytochrome c's*

| | Horse Heart | Tuna Heart | Baker's Yeast |
|---|---|---|---|
| Crown Ethers (mol:mol ratio) | | | |
| Dicyclohexano-18-Crown-6 | | | |
| (1:1) | $1.43 \times 10^4$ (19%) | $2.48 \times 10^4$ (14%) | $3.57 \times 10^4$ (21%) |
| (2:1) | $1.52 \times 10^4$ (31%) | $2.20 \times 10^4$ (27%) | $1.88 \times 10^4$ (21%) |
| (3:1) | $1.53 \times 10^4$ (39%) | — | — |
| Averages: | $1.49 \times 10^4$ (30%) | $2.34 \times 10^4$ (21%) | $2.73 \times 10^4$ (21%) |
| 18-Crown-6 | | | |
| (1:1) | $1.87 \times 10^3$ (13%) | $1.90 \times 10^4$ (11%) | $1.93 \times 10^4$ (26%) |
| (2:1) | $2.88 \times 10^3$ (33%) | $9.96 \times 10^3$ (31%) | $1.23 \times 10^4$ (7%) |
| (3:1) | $1.82 \times 10^3$ (19%) | — | — |
| Averages: | $2.19 \times 10^3$ (22%) | $1.45 \times 10^4$ (21%) | $1.58 \times 10^4$ (17%) |
| Dibenzo-18-Crown-6 | | | |
| (1:1) | $6.95 \times 10^2$ (30%) | $2.35 \times 10^3$ (13%) | $5.41 \times 10^3$ (21%) |
| (2:1) | $6.70 \times 10^2$ (43%) | $1.93 \times 10^3$ (160%) | $4.58 \times 10^3$ (16%) |
| (3:1) | $3.32 \times 10^3$ (44%) | — | — |
| Averages: | $1.56 \times 10^3$ (39%) | $2.14 \times 10^3$ (87%) | $5.00 \times 10^3$ (19%) |

*The relative percent error is given in parentheses next to the calculated $K_B$ values.

Prior work conducted by others has suggested that the protonated lysine residue is the binding site for the crowns. Our computational work has been carried out to better understand the competition that lysine provides for $H_3O+$, $NH_4+$ and the other basic protonated amino acid residues, arginine and histidine (FIGS. 18A–18C). The binding of crowns to the molecules in the solvent system was thus also evaluated.

Figure 19:
FIG. 19 shows the Brookhaven protein database xray crystal structure of tuna (Albacore) cytochrome c with only the basic amino acids attached to a ribbon backbone and an 18-crown-6 shown complexed with a protonated lysine residue.

Cytochrome c is a small protein of about 12,500 Daltons, the molecular weight of which varies slightly with the animal or plant species. The surface of cytochrome c has a number of basic amino acids which are protonated at pH7 when the sample is prepared for ES/MS. FIG. 19 show the Brookhaven crystal structure of Tuna (Albacore) cytochrome c with only the basic amino acids, the heme group and ribbon backbone being shown for reference. In FIG. 19, it can be seen where the crown ethers tend to bind to the positively charged residues present on the protein surface.

The data in this experiments was acquired using an Extrel ELQ 400 single quadrupole mass spectrometer coupled with the novel electro spray source of the invention. The molecular ions formed from the protein are characterized in the mass spectra by multiple distinct charge states ranging from +20 to +6 depending on the experimental conditions and number of available protonation sites.

It appears from the experimental data that protein/neutral complexes may be structurally revealing and/or ES enhancing. In either case it is important to apply computational methods to clarify the nature of this binding. The semi-empirical quantum mechanics package, MOPAC (ver. 5.0), with the AM1 Hamiltonian, has been used in conjunction with the molecular modeling package SYBYL (ver. 5.4), running under VAX/VMS (ver. 5.5), in order to determine the heats of formation of the hydrogen bonded crown/cation complex. The molecules were built, merged, annealed and then minimized using the Sybyl Maximin 2 molecular mechanics forcefield. The resultant molecules and complexes were then geometrically optimized using MOPAC/AM1 and the Heats of Formation (see FIGS. 20A–20F) used with Hess's Law to determine relative stability of the complexes.

A comparison of experimental values versus calculated values for $\Delta H_f$ is given below in Table 2.

TABLE 2

Thermodynamic Values for Small Molecules/Ions (kcal/mol)

| | $\Delta H_f$ | $\Delta H_f$ | | PA | PA |
|---|---|---|---|---|---|
| Molecule | (calc.) | [exp.] | (conj. acid) | (calc.)* | (lit.) [2] |
| $H_2O$ | −59.2 | [−57.8] | 143.5 | 164.5 | 170.3 |
| $HOCH_3$ | −57.0 | [−48.1] | 138.3 | 171.9 | 182.2 |
| $NH_3$ | −7.3 | [11.0] | 150.6 | 209.3 | 202.3 |

*$\Delta H_f$ ($H^+$) = 367.1 (JANAF Tables)

The application of Hess's Law to the stability of crown binding to the systems of interest was carried out and a representative sample of the results is shown below in Table 3.

TABLE 3

I.
18-Crown-6/$H_3O^+$ + $NH_3$ ---> 18-Crown-6/$NH_4+$ + $H_2O$
  −203.36       −7.28        −184.87       −59.24
Heat of Reaction = −33.47 kcal/mol
II.
18-Crown-6/$CH_3OH_2$+ + $H_2O$ ---> 18-Crown-6/$H_3O^+$ + $CH_3OH$
  −191.31       −59.24        −203.36       −57.03
Heat of Reaction = −9.84 kcal/mol
III.
18-Crown-6/$CH_3OH_2$+ + Lys ---> 18-Crown-6/$Lys^+$ + $CH_3OH$
  −191.31       −116.31        −294.96       −57.03
Heat of Reaction = −44.37
IV.
18-Crown-6/$H_3O^+$ + Lys ---> 18-Crown-6/$Lys^+$ + $H_2O$
  −203.36       −116.31        −294.96       −59.24
Heat of Reaction = −34.53 kcal/mol
V.
18-Crown-6/$H_3O^+$ + Arg ---> 18-Crown-6/$Arg^+$ + $H_2O$
  −203.36       −75.13        −249.25       −59.24
Heat of Reaction = −30.00 kcal/mol
VI.

TABLE 3-continued

Dibenzo-18-Crown-6/H$_3$O$^+$ + Lys -> Dibenzo-18-Crown-6/Lys$^+$ +H$_2$O
    −106.62        −116.31        −194.52        −59.24
Heat of Reaction = −30.83
VII.
Dicyclohexyl-18-Crown-6/H$_3$O$^+$ + Lys ->
Dicyclohexyl-18-Crown-6/Lys$^+$ + H$_2$O
  −233.14    −116.31    −325.12    −59.24
Heat of Reaction = −34.91

Figure 21:
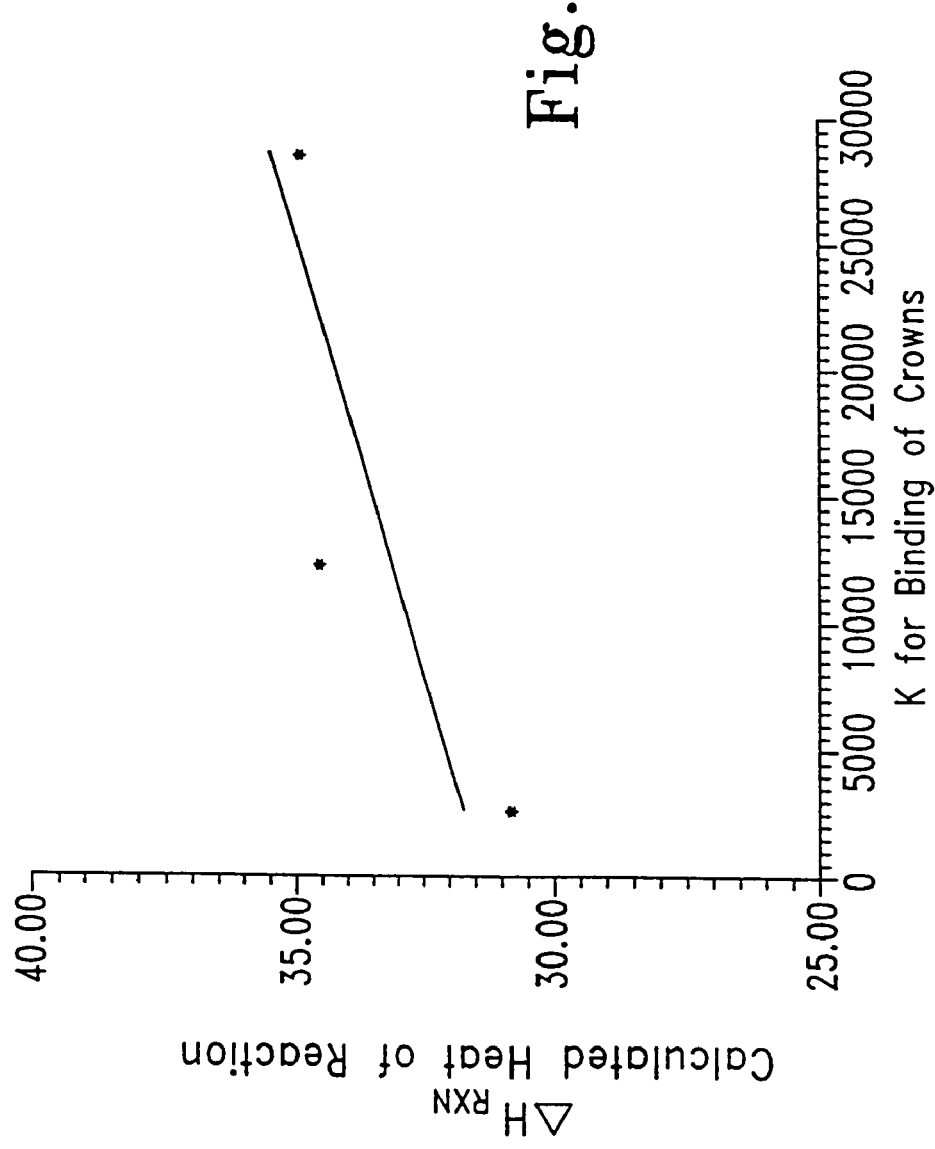
FIG. 21 is a graphical presentation of the linear plot of the trend for the calculated heats of reaction following that of the experimentally determined K for the binding of crown ethers to cytochrome c.

The calculated heats of formation indicate that little complex formation occurs with the molecules form the ES/MS solvent system, a water/acetic acid and methanol mixture. (The solvent system molecules of interest being hydronium ion and protonated methanol.) From Table 3 (eq. II.), the complex of 18-crown-6 with hydronium ion is favored over protonated methanol by −9.8 kcal/mol. The 18-crown-6/lysine$^+$ complex is favored over both protonated methanol and hydronium ion (eq. III and IV) as are the other two amino acids, arginine and histidine (eq. V). The complex of 18-ammonium ion by −1.06 kcal/mol; however, formation of complexes of 18-crown-6 with arginine (+3.47 kcal/mol) and histidine (+70.13 kcal/mol) both are less exothermic than the reaction of crown with the ammonium iron. Optimized structures modeling the complexes of protonated amino acids with 18-crown-6 and dibenzo-18-crown-6 are shown in FIG. 20. The $\Delta H_f$ formed combines lysine with sicyclohexyl-18-crown-6 (−34.91 kcal/mol, eq. IV), dibenzo-18-crown-6 (−30.53 kcal/mol, eq. VI). The trend for the calculated $\Delta H_{RXN}$ follows that of the experimentally determined K for the binding of crown ethers to cytochrome c, the linear plot for which is shown in FIG. 21. The calculations presented in Table 2, considered in combination with the data presented in FIGS. 8 and 19, confirm for the first time that crown ethers do in fact attach to positive residues present on the protein surface. This phenomenon had only been speculated prior to this invention.

Example Two and Tables 2 and 3 presented above show that the binding constants calculated experimentally by ES-MS are, in facts, different when using different crown ethers and different cytochrome c's. This is rationalized by thinking of the protein surface as being topologically complex. The method of this invention assumes that the crown ethers bind at quaternary amines (protonated amino groups) on the surface of the protein molecule. There exist many different topologically accessible quaternary amines on a protein's surface, those attributed to protonated forms of the basic amino acids, such as lysine, arginine and histidine, in addition to those of the terminal amino group of the particular protein. These amino acids are typical components in any protein. The computations performed by the molecular modeling program employed herein predicted that the most stable complexes would be complexes of protonated lysine with crown ethers. This was confirmed by the experimentally determined binding constants. Therefore, a model predicting the potential for binding at these quaternary amines is extremely useful.

As described in Example Two, the experimentally determined binding constants of various crown ethers to cytochrome c were compared to the heats of formation calculated using a general computational molecular model program for the binding of the same crown ethers to various protonated residues. As noted, this program predicted that the most stable complexes would be complexes of protonated lysine with crown ethers, and this prediction was confirmed by the experimentally determined binding constants. In fact, a plot of the experimentally determined binding constants against the calculated heats of reaction for three crown ethers binding to cytochrome c shown in FIG. 21 show a linear relationship between the experimental and calculated binding energies.

While the computational molecular model programs utilized in Example Two do not include molecular models of complete proteins, the existence and content of such programs are well known in the art. Such programs include SYBYL (Tripos, Inc.—St. Louis, Mo.) and INSIGHT II (Biosym/MSI—San Diego, Calif.). Moreover, those ordinarily skilled in the art, using the guidance provided by this specification, would readily understand how such programs could be utilized to characterize the three-dimensional structure of proteins, including determining the binding potential of specific protein residues. A specific modeling package presently available is INSIGHT II/QuanteMM.

Characterizing the protein surface by comparing experimentally determined data for the binding of small molecules to the protein surface with data from a computer model allows one to determine their fit to a straight line, as a first approximation. This yields a basic model whose method can then be applied generally. In the method of my present invention, the experimental determination of the small-molecule binding constant to the protein is considered a numerical solution to an unknown experimental function. Being able to determine the binding constant without actually conducting the experiment is possible by running a computer program simulating the physical experiment. The computer generated result can be verified by comparison to experimental data. I refer to this method as an experimental/computational feedback loop.

A well-recognized advantage that a computer has is its ability to store many more pieces of information than is possible with a manual approach. The best solution would be to have the computer simulate the real-world problem using a specially designed program. The molecular modeling programs described above do just that, with some limitations, for chemical and biological systems.

A problem with utilizing a computer to run a simulation of an experiments is that often the "time constant" of the experiment is such that much more time is needed for the computer to run a simulation of the experiment. With today's faster computers and better algorithms, this problem can now be somewhat minimized. Indeed, it is now possible for many computer simulations to be performed in nearly equal time as the actual physical experiment. Consequently, the unknown function whose solution has previously been determined from physical experiment can now be determined by computer simulation. The program's results are reported within a certain statistical error, as experimental results typically are.

It is now commonplace in science and engineering to compare real-world experimental data with computer models (static results) and simulations (dynamic results) of the physical experiments.

Most kinds of scientific experimentation yield results that do not have a computational analog, i.e., where a computer program exists to use the data for modeling or simulation. A problem then arises in that, only after numerical analysis or some other type of interpretation, is one able to find a function that will unambiguously describe the unknown function that the experiment was designed to reveal. It is common that the data are not as revealing as one would have wished, and new experiments need then be designed. The interpretation of experimental results are, thus, not always clear-cut. The novel method described herein, the characterization of a protein surface, is performed by "fitting" the experimental results to computational results. My described method is a novel and new invention as applied to the study of protein characterization.

Figure 22:
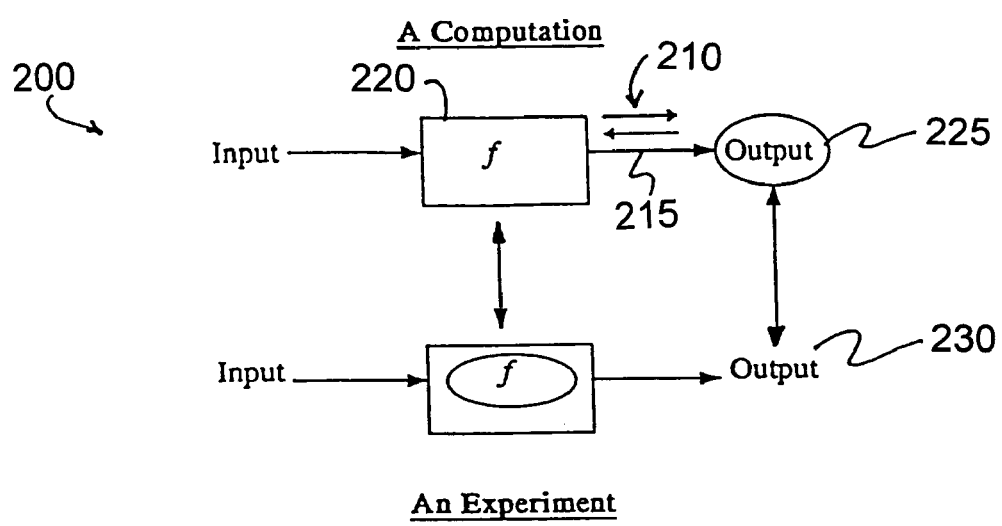
FIG. 22 is a schematic diagram of a computational feedback model utilized by this invention to compare experimental data with simulated data to determine an experimental unknown.

In a more general case, in the experimental/computational feedback loop shown and described in relation to FIG. 22, the active comparison of an ongoing experiment with a computer simulation of the same experiment can facilitate the determination of the experimental unknown by "fitting" this data to a computer simulation. Some types of experimental data may be better suited to this method, but all forms of experimental results are amenable. In the protein characterization method described herein, the experimental numerical analysis was performed with "pencil and paper" (but only because a computer program to carry out the numerical analysis was not available). Such a program is readily available or can be easily written by one ordinarily skilled in the art. Next, a computer model is made using a molecular modeling program to mimic or model the experiment, using certain assumptions to simplify the initial model design. In my research, this computer model provided visual and numerical results. Then, the two numerical results (the experiment provided no visual model of the results) are compared using linear regression. When the "fit" (coefficient) between the experimental data and the computer data results in a "good fit" (a high correlation coefficient), one can conclude that a match or an identity exists between the two sets of data. The experimental unknown (in the specific case, which type of amino acid residue (arginine, lysine, or histidine) is complexed by a crown ether and is identified, in part, because of its close match to the independently determined computational model, which gives a visualization of the chemical structure, and it numerical result.

Straightforward programming can be written connecting all of these pieces of data. The experimental data can be stored directly as a computer file, along with the computational data from a modeling or simulation program. From the computational data derived from the model, the numerical analysis and comparison could be performed, fitting the data and providing the final result as a visualization (and/or graph and tabulated data) on the computer. This can be done so that the experimental data provides information to the computer as the experiment is being performed (i.e., in real-time).

It can now be understood how this modeling method can be used to further advantage. The method can even be enhanced through additional programming, well known to those familiar in the art, to allow the experimental data to, directly and in real-time, modify the computer model so that the model becomes a dynamic system simulating the experiment and is continuously modified by the experiment through continuous "feedback" of experimental data. This allows the computer to find the best fit (not necessarily an linear fit) to the experimental data as the experiment is being performed. In a preferred embodiment, the difference in the time-constant between the experiment and the speed of the computer simulation is small. As a result, the time lag between the experiment and the computer simulation will appear to be, nearly, real-time. This is defined in this patent application as a "feedback loop."

If the information flows from the experiment to the computer simulation only (or visa versa), this is defined as a "undirectional feedback loop". A further embodiment exists where the computer simulation sends its information directly to the experimental apparatus in order for the experimental parameters to be modified by the computer simulation to, for example, find the experimental conditions needed to better fit a desired computer model. The flow of data in both directions, generated by either the experiment or the computer simulation, is defined as a "bi-directional feedback loop." This latter scenario is the general case for the method described herein for the comparison of experimental data to a computer simulation.

The realization of the utility of this general approach derives directly from the specific application of characterizing the protein surface using both experimental and computational methods. Although this method is well within the grasp of those knowledgeable in the art, it has never, to the best of my knowledge, been described or implemented prior to this disclosure. Its application in the chemical field is of most beneficial use in that it is difficult to directly visualize chemical structures. While the usual methods of experimentation and data interpretation are typically done in such a manner that an accurate static or dynamic chemical system can be visually described, the great utility of this invention can be realized by virtue of its inherent ability to determine and represent solutions to experimental unknowns using the scientific visualization and graphical software already used for modeling and simulations. Experimental analyses can be presented visually, in terms of the molecules, structures or drawings already in use. Instrumentation can be designed to make use of the bi-directional feedback loop providing virtually automated experimental data collection, analysis and interpretation, and providing tabulated data as well as graphical models and dynamic visual presentation of data from a combined experimental/computational system. The schematic shown in FIG. 22 represents this experimental/computational feedback loop provided by my invention.

Thus, this invention also provides a method for aiding in the solution of experimental unknowns using experimental/computational feedback, comprising the steps of (a) performing a physical experiment on a predetermined system, (b) acquiring raw experimental data with selected instrumentations and digitizing the data (the raw experimental data may consist of a few or a very large number of datum), (c) storing the digitized data in a computer memory, (d) initializing and running a pre-selected computer program for modeling or simulating the physical experiment being performed in the initial step, (e) using the digitized experimental data to compute a new result for the computer simulation of the experiment, the results of which are also stored in a memory, (f) comparing the new result from the physical experiment, (g) replacing the undefined parameters from the experiment with the explicit parameters assumed in the computer simulation, if the result is found to be within a predetermined parameter, and (h) if the result is found to be outside a predetermined parameter, establishing a feedback loop and initiating an iterative subroutine whereby the computer simulation adjusts itself, in an incremental way, to fit the simulation to the experimental value, compares the result to the experimental results after each computational step and feeds the experimental data back into the input loop of the computer simulation until the result of the comparison is found to be within a predetermined parameter. This can be considered as a self-correcting computer simulation based on experimental input.

Steps (g) and (h) are considered to be a unidirectional feedback loop. A simple example might be that, if the experiment gives only a particular energy, and the computer simulation gives the same energy, then other related parameters in the simulation can be applied to the experiment, e.g., a particular angle and length that is associated with that energy in the simulation can then be used to define that particular angle and length that were previously unknown in the experiment. This is an example of a solution to an experimental unknown determined from the computer simulation of the experiment.

A bi-directional feedback loop is described by a computer simulation that, when a comparison is not realized, feeds back to the experimental instrumentation a signal controlling an experimental parameter, e.g., temperature or pressure, thereby producing an new set of data that can be compared, again, to the computational simulation result. The computer simulation then creates for itself variable parameters that it adjusts while comparing its result to the experimental data. The computer simulation could then, e.g., iterate through temperature, pressure and energy variables to attempts a match with the experimental data. When a successful comparison occurs, the assumed parameters explicitly stated in the simulation can be substituted for unknown parameters in the experimental system. In this way, the computer simulation can be used to solve for unknowns in the experimental system, while feeding back experimental data that allows the computer simulation to be representative of the experimental system. The final result is a computer model or simulation that has been empirically corrected by experiment.

The feedback circuit 200 shown in FIG. 22 is bi-directional, and the unknown is each case is enclosed by an ellipse. It is assumed that the computation is running a simulation of the experiment. The double arrows 210 above the output arrow 215 of the computation 220 indicate that an iterative routine could be used, in the computation 220, to approach an output value 225 correlating with the experimental output 230. When a good correlation is obtained, the computational function, simulating the experiment, can be used to solve the experimental unknown.

For example, a program which contains or can produce a model of the three-dimensional structure of a protein of interest can readily be selected by one ordinarily skilled in the art. Then, the protein of interest is reacted with several different small molecules (e.g., several different crown ethers), and the ES-MS spectra of the protein-small molecule complexes is obtained, all as described in Examples 1 and 2. The binding constants ($K_B$) for the binding of the small molecule to the protein can then be determined experimentally from the ES-MS spectrum as described in this disclosure. Next, the heats of formation ($\Delta H_f$) for the binding of each of the different small molecules to, e.g., each protonated amino group and associated nearby interactions, predicted by the computer model to be on the surface of the protein molecule are calculated using the computer model, as indicated above. The calculated and experimentally determined binding energies are then compared to characterize the three-dimensional structure of the protein by specifically locating on the protein surface amino acid residues that interact in only one unique way with the set of binding ligands (e.g. crown ethers).

For instance, the calculated and experimentally determined binding energies are compared by plotting the ($K_B$) values versus the ($\Delta H_{RXN}$) values for the binding of the small molecules to a selected protonated amino group on the protein. A similar plot can be constructed for each of the other identified protonated amino groups. The plot(s) giving the best linear fit(s) identify the amino acid residue(s) to which the small molecules are binding and which is (are) most accessible for binding by other small molecules. In addition, deviation of any of the plots from linearity indicates that the computer model of the three-dimensional structure is incorrect, and the three-dimensional model is adjusted until a plot giving a-good linear fit is obtained. In this manner, the model of the three-dimensional structure of the protein of interest can be refined to fit the experimental data.

As noted above, the binding of crown ethers to a protein molecule appears to cause a change in the conformation of the protein that can be observed in the ES-MS spectra. This phenomenon has not been previously reported as having been observed. When crown ethers bind to protein molecules, the surface hydrophobicity of the protein molecules is increased thereby, and this change in hydrophobicity may explain the change in molecular conformation that appears to be observable in the mass spectra. This is a very valuable discovery in that numerous drugs work by changing the conformation, and thereby the function of, proteins at the molecular level. The method of the present invention claimed below can be utilized to identify the residue(s) of a protein to which a small molecule is bound and to predict the potential of binding of small molecules to the protein.

In a preferred embodiment of the invention, crown ethers were used as discussed above. However, other types of small molecules that bind to the protonated amino groups of proteins can be used. To one of ordinary skill in the art, such small molecules would include crown ethers, other macrocyclic polyethers, cryptands, and polymers of these compounds. One ordinarily skilled in the art will recognize the binding or complexation of individual functional groups or collections of groups on macromolecular structures may be accomplished by any number of different ligands. The scope of this invention includes all such events which may be subject to the method described and claimed herein.

Applicant has concluded that the crown ether molecules bind to the positively charged amino acid residues on the surface of the protein molecules, thereby changing its three-dimensional structure and increasing the hydrophobicity of the protein surface, which results in the protein surface being more non-polar. With this invention, it is now possible to bind small molecules to charged residues on the protein surface, which would then allow a desirable modification of a protein's function. More particularly, this invention provides the ability to locate positively charged residues on the surface of a protein by identifying or locating groups that may become attached to the crown ether(s). These newly attached functions can alter the function and character of the protein either directly or indirectly. This aspect is significant in pharmaceutical research and development because drugs perform primarily by modifying the manner in which proteins perform physiologically. Accordingly, it is important in such research to be able to focus on what binds to proteins to determine how to modify their behavior. This invention provides that ability to locate positively charged residues on the surface of a protein by identifying or locating groups that may become attached to the crown ether(s). As indicated above, it is these newly attached functions that can alter the function and character of the protein.

While the method described above constitutes a presently preferred embodiment of the invention, the invention can take many forms. Accordingly, it should be understood that the invention is to be limited only insofar as is required by the scope of the following claims.

I claim:

1. A method for characterizing the three-dimensional structure of a large molecule comprising the steps of:
    (a) mixing a small molecule with a large molecule so that the small molecule binds non-covalently to the large molecule to form a large molecule-small molecule complex;

(b) performing electrospray ionization mass spectrometry to obtain the spectrum of the large molecule-small molecule complex;

(c) repeating steps (a)–(b) with additional different small molecules; and (d) utilizing the spectra obtained in steps (a)–(c) to characterize the three-dimensional structure of the large molecule, wherein the three-dimensional structure characterization of step (d) is carried out by feedback modeling according to the following steps:

(e) providing data processing means;

(f) providing data storage means;

(g) digitizing raw experimental data acquired according to steps (a)–(c);

(h) storing the digitized data in said data storage means;

(i) initializing and running a selected computer program on said data processing means for simulating the experiment performed in steps (a)–(c);

(j) comparing simulation data obtained from step (i) with the digitized data from the experiment performed in step (g);

(k) if the comparing step (j) produces a result outside a predetermined parameter, establishing a feedback loop and initiating an iterative subroutine whereby the computer simulation adjusts itself, in an incremental way, to fit the simulation to the experimental value, compares the result to the experiment after each computational step and feeds the experimental data back into the input loop of the computation until the result of the comparison of step (i) is within the predetermined parameter.

2. The large molecule characterization method of claim 1, wherein the large molecule is selected from the group consisting of polypeptides, proteins, DNA, RNA, oligosaccharides, and polymers thereof.

3. The large molecule characterization method of claim 1, wherein the small molecules include crown ethers, macrocyclic polyethers, cryptands, and/or polymers of these compounds, or any other suitable ligand or macrocyclic ligand.

4. A method for characterizing the three-dimensional structure of a large molecule comprising the steps of:

(a) mixing a small molecule with a large molecule so that the small molecule binds non-covalently to the large molecule to form a large molecule-small molecule complex;

(b) performing electrospray ionization mass spectrometry to obtain the spectrum of the large molecule-small molecule complex, (c) using the spectrum from step (b) to calculate the binding constant KB for the binding of the small molecule complex;

(d) repeating steps (a)–(c) with additional different small molecules;

(e) calculating the heat of formation ($\Delta H_f$) for the binding of each of the small molecules used in steps (a)–(d) to a selected residue on the large molecule;

(f) repeating step (e) for other selected residues on the large molecule;

(g) comparing the binding constants ($K_B$) calculated in steps (c) and (d) with the $\Delta H_f$ values calculated in steps (e) and (f); and (h) utilizing the comparisons of step (g) to characterize the three-dimensional structure of the large molecule, wherein said comparing step (g) is carried out by feedback modeling according to the following steps:

(i) providing data processing means;

(j) providing data store means;

(k) digitizing raw experimental data acquired according to steps (a)–(d);

(l) storing the digitized data in said data storage means;

(m) initializing and running a selected computer program on said data processing means for simulating the three-dimensional structure of said large molecule according calculations performed in steps (e)–(f);

(n) comparing simulation data obtained from step (m) with the digitized data from the experiment performed in step (k);

(o) if the comparing step (n) produces a result outside a predetermined parameter, establishing a feedback loop and initiating an iterative subroutine whereby the computer simulation adjusts itself, in an incremental way, to fit the simulation to the experimental value, compares the result to the experiment after each computational step and feeds the experimental data back into the input loop of the computation until the result of the comparison of step (n) is within the predetermined parameter.

5. The large molecule characterization method of claim 4, wherein the comparisons of step (g) are utilized to identify the residue or residues on the surface of the protein molecule to which the small molecule is bound.

6. The large molecule characterization method of claim 5, wherein the large molecule is selected from the group consisting of polypeptides, proteins, DNA, RNA, oligosaccharides, and polymers thereof.

7. The large molecule characterization method of claim 5, wherein the small molecules include crown ethers, macrocyclic polyethers, cryptands, and/or polymers of these compounds, or any other suitable ligand or macrocyclic ligand.

8. The large molecule characterization method of claim 4, wherein the large molecule is selected from the group consisting of polypeptides, proteins, DNA, RNA, oligosaccharides, and polymers thereof.

9. The large molecule characterization method of claim 4, wherein the small molecules include crown ethers, macrocyclic polyethers, cryptands, and/or polymers of these compounds, or any other suitable ligand or macrocyclic ligand.

10. The large molecule characterization method of claim 4, further comprising the step of using the heat of formation calculated in step (e) and calculating the heat of reaction ($\Delta H_{RXN}$) for the binding of each of the small molecules used in steps (a)–(d) to a selected residue on the large molecule.

11. The large molecule characterization method of claim 10, wherein the large molecule is selected from the group consisting of polypeptides, proteins, DNA, RNA, oligosaccharides, and polymers thereof.

12. The large molecule characterization method of claim 10, wherein the small molecules include crown ethers, macrocyclic polyethers, cryptands, and/or polymers of these compounds, or any other suitable ligand or macrocyclic ligand.

* * * * *